United States Patent
Shadie et al.

(10) Patent No.: US 10,792,448 B2
(45) Date of Patent: Oct. 6, 2020

(54) MOTOR DRIVE SYSTEM FOR RESPIRATORY APPARATUS

(71) Applicant: ResMed Pty Ltd, Bella Vista, NSW (AU)

(72) Inventors: Timothy Nicholas Shadie, Bella Vista (AU); James McKensey Bencke, Bella Vista (AU)

(73) Assignee: ResMed Pty Ltd (AU)

( * ) Notice: Subject to any disclaimer, the term of this patent is extended or adjusted under 35 U.S.C. 154(b) by 1015 days.

(21) Appl. No.: 14/900,899

(22) PCT Filed: Jun. 20, 2014

(86) PCT No.: PCT/AU2014/050085
§ 371 (c)(1),
(2) Date: Dec. 22, 2015

(87) PCT Pub. No.: WO2015/000025
PCT Pub. Date: Jan. 8, 2015

(65) Prior Publication Data
US 2016/0375209 A1    Dec. 29, 2016

Related U.S. Application Data

(60) Provisional application No. 61/841,650, filed on Jul. 1, 2013.

(51) Int. Cl.
*A61M 16/00*    (2006.01)
*A61M 16/06*    (2006.01)
(Continued)

(52) U.S. Cl.
CPC .... *A61M 16/0066* (2013.01); *A61M 16/0051* (2013.01); *A61M 16/0069* (2014.02);
(Continued)

(58) Field of Classification Search
CPC ............ A61M 16/0066; A61M 16/024; A61M 16/0069; A61M 2205/8237;
(Continued)

(56) References Cited

U.S. PATENT DOCUMENTS 3,365,617 A    1/1968    Flanagan
3,551,781 A *  12/1970   Smith ............... H02M 7/062
                                                    363/128
(Continued)

FOREIGN PATENT DOCUMENTS

CN          1551477 A      12/2004
CN          102209569 A    10/2011
(Continued)

OTHER PUBLICATIONS

TVS Diode Catalog, 2008, Little Fuse, pp. 4-7 (Year: 2008).*
(Continued)

*Primary Examiner* — Samchuan C Yao
*Assistant Examiner* — Margaret M Luarca
(74) *Attorney, Agent, or Firm* — Botos Churchill IP Law LLP

(57) ABSTRACT

A respiratory apparatus includes components to protect operations of the apparatus. For example, in some versions, the apparatus may include a power supply, a motor powered by the power supply, and a transient absorption diode circuit between the motor and the power supply. The transient absorption diode circuit may be configured to absorb energy generated by the motor from rotational kinetic energy. Such absorption may serve to protect the components of the apparatus. In some examples, the apparatus may include a fault mitigation integrated circuit (IC). The IC circuit may be included in the respiratory apparatus to detect one or more faults based on physical and system parameters of the apparatus. The fault mitigation integrated circuit may gen- (Continued)

erate a signal to stop the motor based on the detected fault, and may digitally communicate with a processor information about the detected fault.

20 Claims, 18 Drawing Sheets

(51) Int. Cl.
    *A61M 16/16*     (2006.01)
    *F04D 27/00*     (2006.01)
    *A61M 16/10*     (2006.01)
    *A61M 16/20*     (2006.01)
    *H02P 6/14*     (2016.01)
    *H02P 6/24*     (2006.01)
    *H02P 27/06*     (2006.01)

(52) U.S. Cl.
    CPC .......... *A61M 16/024* (2017.08); *A61M 16/06* (2013.01); *A61M 16/105* (2013.01); *A61M 16/16* (2013.01); *A61M 16/20* (2013.01); *F04D 27/004* (2013.01); *H02P 6/14* (2013.01); *H02P 6/24* (2013.01); *H02P 27/06* (2013.01); *A61M 16/0683* (2013.01); *A61M 16/107* (2014.02); *A61M 16/1055* (2013.01); *A61M 2016/003* (2013.01); *A61M 2016/0027* (2013.01); *A61M 2016/0033* (2013.01); *A61M 2202/0208* (2013.01); *A61M 2205/15* (2013.01); *A61M 2205/17* (2013.01); *A61M 2205/21* (2013.01); *A61M 2205/3365* (2013.01); *A61M 2205/3368* (2013.01); *A61M 2205/3553* (2013.01); *A61M 2205/3561* (2013.01); *A61M 2205/3584* (2013.01); *A61M 2205/3592* (2013.01); *A61M 2205/42* (2013.01); *A61M 2205/50* (2013.01); *A61M 2205/7545* (2013.01); *A61M 2205/82* (2013.01); *A61M 2205/8237* (2013.01)

(58) Field of Classification Search
    CPC .......... A61M 2205/3365; F04D 27/004; H02P 27/06; H02P 6/24; H02P 6/14; H02P 6/00
    See application file for complete search history.

(56) References Cited

U.S. PATENT DOCUMENTS

| | | | |
|---|---|---|---|
| 3,634,874 A * | 1/1972 | Mason | H02P 25/10 388/819 |
| 4,944,310 A | 7/1990 | Sullivan | |
| 4,971,052 A | 11/1990 | Edwards | |
| 5,606,232 A | 2/1997 | Harlan et al. | |
| 5,744,921 A | 4/1998 | Makaran | |
| 5,747,954 A | 5/1998 | Jones et al. | |
| 6,532,957 B2 | 3/2003 | Berthon-Jones | |
| 6,532,959 B1 | 3/2003 | Berthon-Jones | |
| 6,591,834 B1 | 7/2003 | Colla et al. | |
| 6,603,273 B1 | 8/2003 | Wickham et al. | |
| 6,745,768 B2 | 6/2004 | Colla et al. | |
| 6,810,876 B2 | 11/2004 | Berthon-Jones | |
| 7,040,317 B2 | 5/2006 | Colla et al. | |
| 7,537,010 B2 | 5/2009 | Colla et al. | |
| 7,659,678 B2 | 2/2010 | Maiocchi | |
| 8,069,854 B2 | 12/2011 | Colla et al. | |
| 8,844,522 B2 | 9/2014 | Hubby | |
| 2006/0174885 A1 | 8/2006 | Aylsworth et al. | |
| 2007/0247091 A1 | 10/2007 | Maiocchi | |
| 2008/0053441 A1 | 3/2008 | Gottlib et al. | |
| 2008/0105257 A1 | 5/2008 | Klasek et al. | |
| 2009/0044805 A1 | 2/2009 | Somaiya et al. | |
| 2010/0101574 A1 | 4/2010 | Bassin | |
| 2010/0292544 A1 | 11/2010 | Sherman et al. | |
| 2011/0018349 A1 | 1/2011 | Rockenfeller et al. | |
| 2011/0068723 A1 * | 3/2011 | Maiocchi | H02M 3/156 318/400.3 |
| 2011/0162647 A1 | 7/2011 | Huby et al. | |
| 2013/0038258 A1 * | 2/2013 | Kameyama | H02P 27/06 318/400.27 |
| 2013/0271056 A1 * | 10/2013 | Bunte | F03D 7/0224 318/503 |

FOREIGN PATENT DOCUMENTS

| | | | |
|---|---|---|---|
| CN | 202076975 U | 12/2011 | |
| EP | 2000675 A2 | 12/2008 | |
| EP | 2143466 A2 | 1/2010 | |
| JP | 55080113 A | 6/1980 | |
| JP | 03289362 A | 12/1991 | |
| JP | 07308087 A | 11/1995 | |
| JP | 2004532666 A | 10/2004 | |
| JP | 2008503272 A | 2/2008 | |
| JP | 2008259861 A | 10/2008 | |
| JP | 2009511218 A | 3/2009 | |
| JP | 2012086024 A | 5/2012 | |
| JP | 2012516204 A | 7/2012 | |
| WO | 0027457 A1 | 5/2000 | |
| WO | 2002053217 | 7/2002 | |
| WO | 2006009939 A2 | 1/2006 | |
| WO | 2007045017 A2 | 4/2007 | |
| WO | 2008028017 A2 | 3/2008 | |
| WO | 2010027282 A2 | 3/2010 | |
| WO | 2010088084 A1 | 8/2010 | |
| WO | WO2011-054038 * | 5/2011 | ............ A61M 16/00 |
| WO | 2012171072 A1 | 12/2012 | |

OTHER PUBLICATIONS

Hartwig, Series Stacking of TVS for Higher Voltages and Power, Aug. 14, 2007 (Year: 2007).*
Second Office Action issued in corresponding CN application No. 201480038473.9 dated Jan. 12, 2018.
Chinese Search Report for Application No. 201480038473.9 dated May 15, 2017.
Japanese Office Action issued in corresponding Japanese application No. 2016-522135 dated May 25, 2018.
Extended European Search Report for Application No. EP14819384.0 dated Feb. 17, 2017.
Partial International Search Report for Application No. PCT/AU2014/050085 dated Aug. 25, 2014.
International Search Report and Written Opinion for Application No. PCT/AU2014/050085 dated Oct. 24, 2014.
International Preliminary Report on Patentability Chapter II for Application No. PCT/AU2014/050085 dated Jul. 21, 2015.
Chinese Fourth Office Action issued in corresponding CN application No. 2014800384739 dated Mar. 1, 2019.
Notice of Opposition in corresponding EP application No. 3017345B1 dated Jul. 11, 2019.
Extended European Search Report issued in EP application No. 18208214.9 dated Apr. 29, 2019.
TVS Diode, Littlefuse, Product Catalog & design Guide, (2008).
Brushed DC Motor Fundamentals, AN905, Microship, (2010).
Tailored ventilation; Philips Respironics A40, (2013).
Transil, transient voltage surge suppressor (TVS); P6KE; Commercial brochure of STMicroelectronics, (Apr. 2012).
Jameco Electronics; SM6T6V8A/220A; Transil™, (Aug. 2001).
SEMTECH SI96-01, Surging Ideas, TVS Diode Application Note, What are TVS Diodes?, (Sep. 2000).
Basic DC Motor Circuits; G. Recktenwald, Portland University, Oct. 25, 2012.
Vishay General Semiconductor; What is a Silicon Transient Voltage Suppressor and how does it work? B. Hartwig; p. 256, Feb. 2, 2007.
BIPAP A30 & BIPAP A40; Service and Technical Reference Manual; Philips Respironics; pp. 1-3; 7-8; 148; 151; 162, Feb. 25, 2013.
The special clipper diode: the bidirectional transil diode; Materiel Electronique, Mar. 27, 2013.

(56) References Cited

OTHER PUBLICATIONS

Bauer, Andre, "Handbook Pro-Studio Software—Software Installation and Registration—Devices and Chip Selection in the Software—Directions for the Programming of Chips—The Hex-Editor nd its Functions = The Burning Menu and the Programming Options", Dec. 31, 2004.

EP Communication and Preliminary Opinion dated Mar. 30, 2020 for EP Application No. 14819384.0.

JP Office Action dated Aug. 4, 2020 for JP Application No. 2019-116933.

* cited by examiner

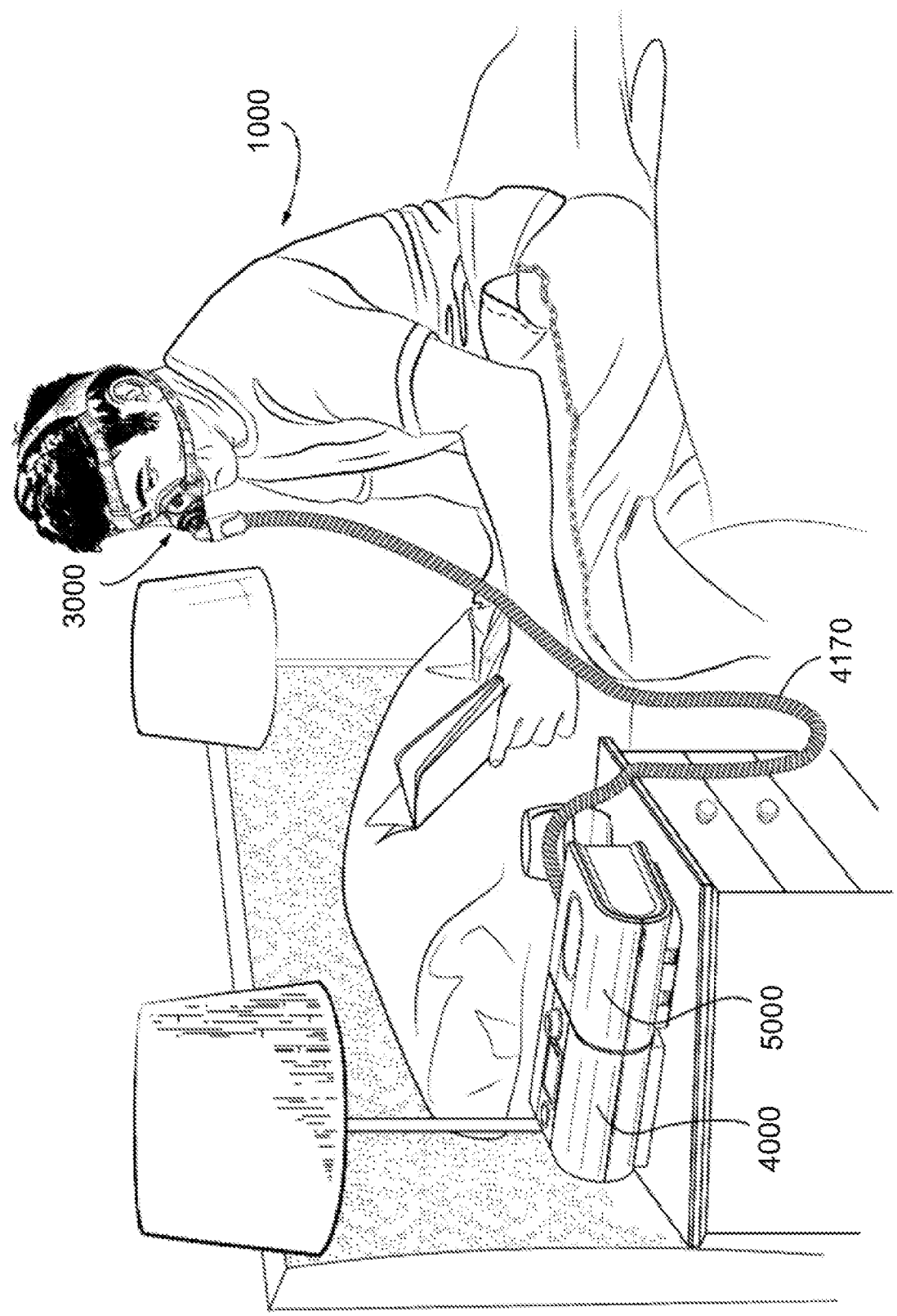

| OUT2 | OUT3 | OUT4 | Fault Type |
|---|---|---|---|
| 0 | 0 | 0 | None |
| 0 | 0 | 1 | Overpressure |
| 0 | 1 | 0 | Under pressure |
| 0 | 1 | 1 | Over temperature |
| 1 | 0 | 0 | Over current |
| 1 | 0 | 1 | Under current |
| 1 | 1 | 0 | Over voltage |
| 1 | 1 | 1 | Under current |

MOTOR DRIVE SYSTEM FOR RESPIRATORY APPARATUS

CROSS-REFERENCE TO RELATED APPLICATIONS

The present application is a national phase entry under 35 U.S.C. § 371 of International Application No. PCT/AU2014/050085 filed Jun. 20, 2014, published in English, which claims priority from U.S. Provisional Patent Application No. 61/841,650, filed Jul. 1, 2013, all of which are incorporated herein by reference.

BACKGROUND OF THE TECHNOLOGY (1) Field of the Technology

The present technology relates to devices for the diagnosis, treatment and/or amelioration of respiratory disorders, and to procedures to prevent respiratory disorders. In particular, the present technology relates to medical devices, and their components, such as for treating respiratory disorders and for preventing respiratory disorders. Such technology may relate to components, for example, protection circuits, that enhance control or operation of such devices such for safety.

(2) Description of the Related Art

The respiratory system of the body facilitates gas exchange. The nose and mouth form the entrance to the airways of a patient.

The airways include a series of branching tubes, which become narrower, shorter and more numerous as they penetrate deeper into the lung. The prime function of the lung is gas exchange, allowing oxygen to move from the air into the venous blood and carbon dioxide to move out. The trachea divides into right and left main bronchi, which further divide eventually into terminal bronchioles. The bronchi make up the conducting airways, and do not take part in gas exchange. Further divisions of the airways lead to the respiratory bronchioles, and eventually to the alveoli. The alveolated region of the lung is where the gas exchange takes place, and is referred to as the respiratory zone. See West, Respiratory Physiology—the essentials.

A range of respiratory disorders exist.

Obstructive Sleep Apnea (OSA), a form of Sleep Disordered Breathing (SDB), is characterized by occlusion or obstruction of the upper air passage during sleep. It results from a combination of an abnormally small upper airway and the normal loss of muscle tone in the region of the tongue, soft palate and posterior oropharyngeal wall during sleep. The condition causes the affected patient to stop breathing for periods typically of 30 to 120 seconds duration, sometimes 200 to 300 times per night. It often causes excessive daytime somnolence, and it may cause cardiovascular disease and brain damage. The syndrome is a common disorder, particularly in middle aged overweight males, although a person affected may have no awareness of the problem. See U.S. Pat. No. 4,944,310 (Sullivan).

Cheyne-Stokes Respiration (CSR) is a disorder of a patient's respiratory controller in which there are rhythmic alternating periods of waxing and waning ventilation, causing repetitive de-oxygenation and re-oxygenation of the arterial blood. It is possible that CSR is harmful because of the repetitive hypoxia. In some patients CSR is associated with repetitive arousal from sleep, which causes severe sleep disruption, increased sympathetic activity, and increased afterload. See U.S. Pat. No. 6,532,959 (Berthon-Jones).

Obesity Hyperventilation Syndrome (OHS) is defined as the combination of severe obesity and awake chronic hypercapnia, in the absence of other known causes for hypoventilation. Symptoms include dyspnea, morning headache and excessive daytime sleepiness.

Chronic Obstructive Pulmonary Disease (COPD) encompasses any of a group of lower airway diseases that have certain characteristics in common. These include increased resistance to air movement, extended expiratory phase of respiration, and loss of the normal elasticity of the lung. Examples of COPD are emphysema and chronic bronchitis. COPD is caused by chronic tobacco smoking (primary risk factor), occupational exposures, air pollution and genetic factors. Symptoms include: dyspnea on exertion, chronic cough and sputum production.

Neuromuscular Disease (NMD) is a broad term that encompasses many diseases and ailments that impair the functioning of the muscles either directly via intrinsic muscle pathology, or indirectly via nerve pathology. Some NMD patients are characterised by progressive muscular impairment leading to loss of ambulation, being wheelchair-bound, swallowing difficulties, respiratory muscle weakness and, eventually, death from respiratory failure. Neuromuscular disorders can be divided into rapidly progressive and slowly progressive: (i) Rapidly progressive disorders: Characterised by muscle impairment that worsens over months and results in death within a few years (e.g. Amyotrophic lateral sclerosis (ALS) and Duchenne muscular dystrophy (DMD) in teenagers); (ii) Variable or slowly progressive disorders: Characterised by muscle impairment that worsens over years and only mildly reduces life expectancy (e.g. Limb girdle, Facioscapulohumeral and Myotonic muscular dystrophy). Symptoms of respiratory failure in NMD include: increasing generalised weakness, dysphagia, dyspnea on exertion and at rest, fatigue, sleepiness, morning headache, and difficulties with concentration and mood changes.

Chest wall disorders are a group of thoracic deformities that result in inefficient coupling between the respiratory muscles and the thoracic cage. The disorders are usually characterised by a restrictive defect and share the potential of long term hypercapnic respiratory failure. Scoliosis and/or kyphoscoliosis may cause severe respiratory failure. Symptoms of respiratory failure include: dyspnea on exertion, peripheral oedema, orthopnea, repeated chest infections, morning headaches, fatigue, poor sleep quality and loss of appetite.

Otherwise healthy individuals may take advantage of systems and devices to prevent respiratory disorders from arising.

The diagnosis of CSR usually involves conducting a sleep study and analyzing the resulting polysomnography ("PSG") data. In a full diagnostic PSG study, a range of biological parameters are monitored that typically include a nasal flow signal, measures of respiratory effort, pulse oximetry, sleeping position, and may include: electroencephalography ("EEG"), electrocardiography ("ECG"), electromyography ("EMG") and electro-oculography ("EOG"). Breathing characteristics are also identified from visual features, thus allowing a clinician to assess respiratory function during sleep and evaluate any presence of CSR. While the examination by a clinician is the most comprehensive method, it is a costly process and depends heavily upon clinical experience and understanding.

Systems

One known product used for treating sleep disordered breathing is the S9 Sleep Therapy System, manufactured by ResMed.

Therapy

Nasal Continuous Positive Airway Pressure (CPAP) therapy has been used to treat Obstructive Sleep Apnea (OSA). The hypothesis is that continuous positive airway pressure acts as a pneumatic splint and may prevent upper airway obstruction by pushing the soft palate and tongue forward and away from the posterior oropharyngeal wall.

Non-invasive ventilation (NIV) has been used to treat CSR, OHS, COPD, MD and Chest Wall disorders. In some cases of NIV, the pressure treatment may be controlled to enforce a target ventilation by measuring a tidal volume or minute ventilation, for example, and controlling the measure of ventilation to satisfy the target ventilation. Servo-controlling of the measure of ventilation, such as by a comparison of an instantaneous measure of ventilation and a long term measure of ventilation, may serve as a treatment to counteract CSR. In some such cases, the form of the pressure treatment delivered by an apparatus may be Pressure Support ventilation. Such a pressure treatment typically provides generation of a higher level of pressure during inspiration (e.g., an IPAP) and generation of a lower level of pressure during expiration (e.g., an EPAP).

Patient Interface

The application of a supply of air at positive pressure to the entrance of the airways of a patient is facilitated by the use of a patient interface, such as a nasal mask, full-face mask or nasal pillows. A range of patient interface devices are known, however a number of them suffer from being one or more of obtrusive, aesthetically undesirable, poorly fitting, difficult to use and uncomfortable especially when worn for long periods of time or when a patient is unfamiliar with a system. Masks designed solely for aviators, as part of personal protection equipment or for the administration of anaesthetics may be tolerable for their original application, but nevertheless be undesirably uncomfortable to be worn for extended periods, for example, while sleeping.

PAP Device

The air at positive pressure is typically supplied to the airway of a patient by a positive airway pressure (PAP) apparatus or device such as a motor-driven blower. The outlet of the blower is connected via a flexible delivery conduit to a patient interface as described above.

Periodic breathing disorders of central origin, such as Cheyne-Stokes respiration, may occur together with upper airway obstruction. The oscillations in central drive to the respiratory musculature may be associated with oscillations in drive to the upper airway musculature, exacerbating any tendency to upper airway obstruction. Any method which attempts to counteract the self-sustaining oscillations in respiratory drive by ventilating the patient, typically with more ventilator drive during periods of low patient effort than during periods of high patient effort, needs the upper airway to be substantially open when it is attempting to deliver ventilatory assistance, otherwise the ventilatory assistance will be to some extent, and often totally, ineffective during the periods of low or zero patient effort, and thus unable to stabilise the patient's ventilation.

This need to keep the upper airway open is typically addressed by attempting to set an expiratory positive airway pressure (EPAP) such that the upper airway is kept open at all times. This may be achieved by some kind of iterative adjustment of EPAP while observing indicators of the patency of the airway at various EPAP levels, in a procedure called a titration. Titration is a skilled and typically expensive operation, preferably being conducted in a sleep laboratory, and may not yield an EPAP sufficient to overcome upper airway obstruction (UAO). Reasons for this include the fact that UAO is often postural, and the patient may never during the titration night assume the posture which produces the worst UAO, typically the supine posture. Sedative and other drugs may variably influence the upper airway. There is also evidence that the degree of cardiac failure affects the degree of upper airway obstruction via oedema of the upper airway. Hence an exacerbation of cardiac failure may worsen upper airway obstruction to an extent which cannot be anticipated during a titration night.

In some cases, methods for evaluating or assessing patient SDB events and/or ventilation may be implemented in such apparatus. The assessment(s) may serve as a basis for control of a generated respiratory pressure treatment. For example, such devices may automatically adjust a level of EPAP in order to counteract upper airway obstruction during respiratory pressure treatment. Similarly, changes in pressure (e.g., a Bi-level treatment with an IPAP and EPAP) may be triggered and cycled to replicate the timing of a patient respiratory cycle or otherwise be synchronized with a detected cycle. Such changes in pressure can result in operational changes of the PAP device that require monitoring.

For example, to ensure proper operation and/or safe use of such PAP devices or other respiratory treatment apparatus, it can be important to implement protection controls. Such control components can provide for safety in the PAP device by detecting or avoiding undesirable or hazardous conditions. Such undesirable or hazardous conditions may include, for example, excess energy, such as that which might occur during braking or sudden deceleration of a motor of the PAP device. Similarly, such components may serve to avoid dangerous over pressure situations. Other examples of undesirable or hazardous conditions may include power failure, transducer malfunction, failure to detect the presence of a component, and operating parameters exceeding the scope of recommended ranges, among other possibilities. Known safety features are typically implemented using complex solutions that require large amounts of printed circuit board (PCB) footprint, labour, and development time, which, in turn, significantly increase the cost per device.

It may be desirable to develop further implementations that simplify the safety solutions, decrease the PCB footprint, labour, development time, and/or the overall cost per device.

BRIEF SUMMARY OF THE TECHNOLOGY

The present technology is directed towards providing medical devices, or the components thereof, that may be used in the detection, diagnosis, amelioration, treatment, and/or prevention of respiratory conditions having one or more of improved comfort, cost, efficacy, ease of use and manufacturability.

Some embodiments of the present technology relate to apparatus used in the detection, diagnosis, amelioration, treatment or prevention of a respiratory disorder.

Some embodiments of the present technology include a respiratory apparatus. The apparatus may include a power supply coupled to a bus and a blower configured to generate a flow of breathable gas. The blower may include a motor powered by the power supply via the bus, and the motor may generate energy at certain times. The apparatus may also include a transient absorption diode circuit on the bus between the motor and the power supply to absorb the energy generated.

In some cases, the respiratory apparatus may also include one or more capacitors between the motor and the power supply to store at least a portion of the energy generated. The motor may be a brushless DC electric motor. The energy generated by the motor may be converted from rotational kinetic energy. The respiratory apparatus may be one of a positive airway pressure or a non-invasive ventilation apparatus.

In some versions, the transient absorption diode circuit may include two or more transient voltage suppressor diodes. The two or more transient voltage suppressor diodes may be connected in series. The transient absorption diode circuit may absorb the generated energy during motor braking. The transient absorption diode circuit may absorb the energy generated for a period of about one or more hundreds of milliseconds. The transient absorption diode circuit may include a first terminal coupled to the direct current line and a second terminal coupled to the ground line.

In some cases, the respiratory apparatus may include a bridge circuit to operate the motor. The transient absorption diode circuit may be connected to the power supply in parallel to the bridge circuit. The bridge circuit may be an inverter bridge. The bridge circuit may include at least one switching MOSFET. The bridge circuit may be configured to decelerate or brake the motor. The respiratory apparatus may include a motor drive coupled to the bridge circuit to control operation of the motor. The motor drive may include a brushless DC motor controller.

In some versions, the power supply may include a Mains powered switched-mode power supply. The Mains powered switched-mode power supply may block negative regenerative currents. The power supply may be coupled to the bridge circuit. A first terminal of the power supply may be coupled to a first terminal of the bridge circuit by a direct current line. A second terminal of the power supply may be coupled to a second terminal of the bridge circuit by a ground line.

Some embodiments of the present technology include a respiratory apparatus. The apparatus may include a blower driven by a motor to generate a flow of breathable gas, and at least one sensor configured to provide at least one input signal indicative of at least one of a physical and system parameter. The at least physical and system parameter may include one or more of a system reset, pressure, motor current, temperature, motor speed, and motor bus voltage signal. The apparatus may include a microprocessor configured to provide executable instructions to control the motor.

The apparatus may also include a fault mitigation integrated circuit in communication with the motor and the microprocessor. The fault mitigation integrated circuit may be configured to receive the at least one input signal from the at least one sensor, detect a fault based on the received at least one input signal, and generate an output signal to stop the motor based on the detected fault.

In some cases, the fault mitigation integrated circuit may be configured to digitally communicate with the microprocessor information representative of the detected fault. The at least one input signal may include at least one of an analog and digital signal. The fault mitigation integrated circuit may include a programmable logic device. The fault mitigation integrated circuit may also include a timer.

In some versions, the fault mitigation integrated circuit may include one or more digital output pins. The fault mitigation integrated circuit may be configured to send a stop signal to interrupt the microprocessor via one of the one or more digital output pins. The fault mitigation integrated circuit may set a binary value on one or more remaining digital output pins to indicate a type of the detected fault. The binary value may be readable by the microprocessor.

In some cases, the output signal generated by the fault mitigation integrated circuit to stop the motor may be a digital signal. The fault mitigation integrated circuit may be configured to latch the signal. The latched signal may be an interrupt to the microprocessor to indicate that a fault has occurred. The fault mitigation integrated circuit may be configured to latch signals at multiple digital output pins to indicate a type of the detected fault. The signals at the multiple digital output pins may represent a binary code.

In some versions, the fault mitigation integrated circuit may be reset when power of the apparatus is cycled. The fault mitigation integrated circuit may also be reset when receiving a system reset signal.

The subject headings used in the detailed description are included only for the ease of reference of the reader and should not be used to limit the subject matter found throughout the disclosure or the claims. The subject headings should not be used in construing the scope of the claims or the claim limitations.

Various aspects of the described example embodiments may be combined with aspects of certain other example embodiments to realize yet further embodiments. It is to be understood that one or more features of any one example may be combinable with one or more features of the other examples. In addition, any single feature or combination of features in any example or examples may constitute patentable subject matter.

Other features of the technology will be apparent from consideration of the information contained in the following detailed description.

BRIEF DESCRIPTION OF THE SEVERAL VIEWS OF THE DRAWINGS

The present technology is illustrated by way of example, and not by way of limitation, in the figures of the accompanying drawings, in which like reference numerals refer to similar elements including:

Treatment Systems

FIG. 1b shows a PAP device in use on a patient with a nasal mask.

Therapy

Respiratory System

Figure 1A:
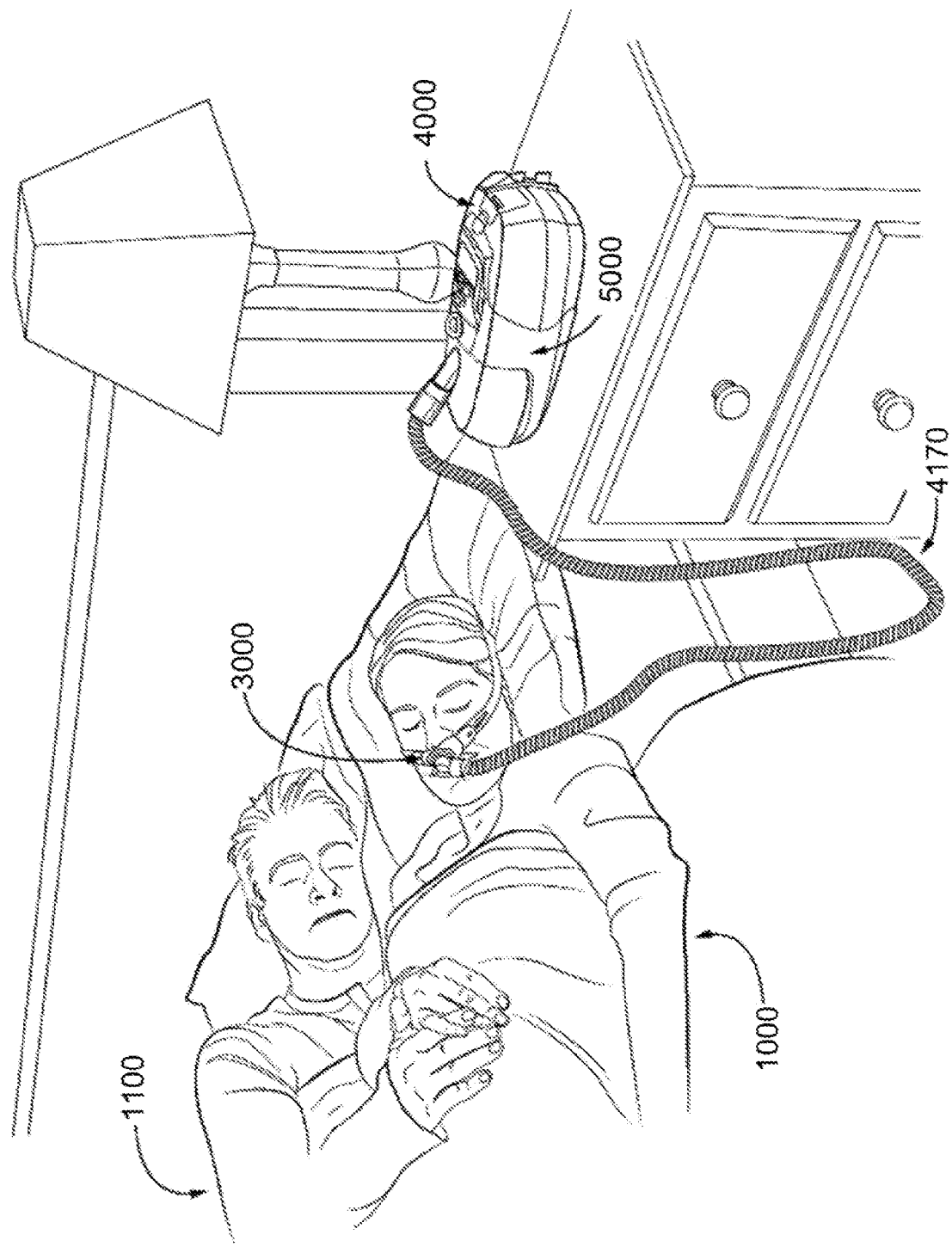
FIG. 1a shows a system in accordance with the present technology. A patient 1000 wearing a patient interface 3000, receives a supply of air at positive pressure from a PAP device 4000. Air from the PAP device is humidified in a humidifier 5000, and passes along an air circuit 4170 to the patient 1000.
Figure 1C:
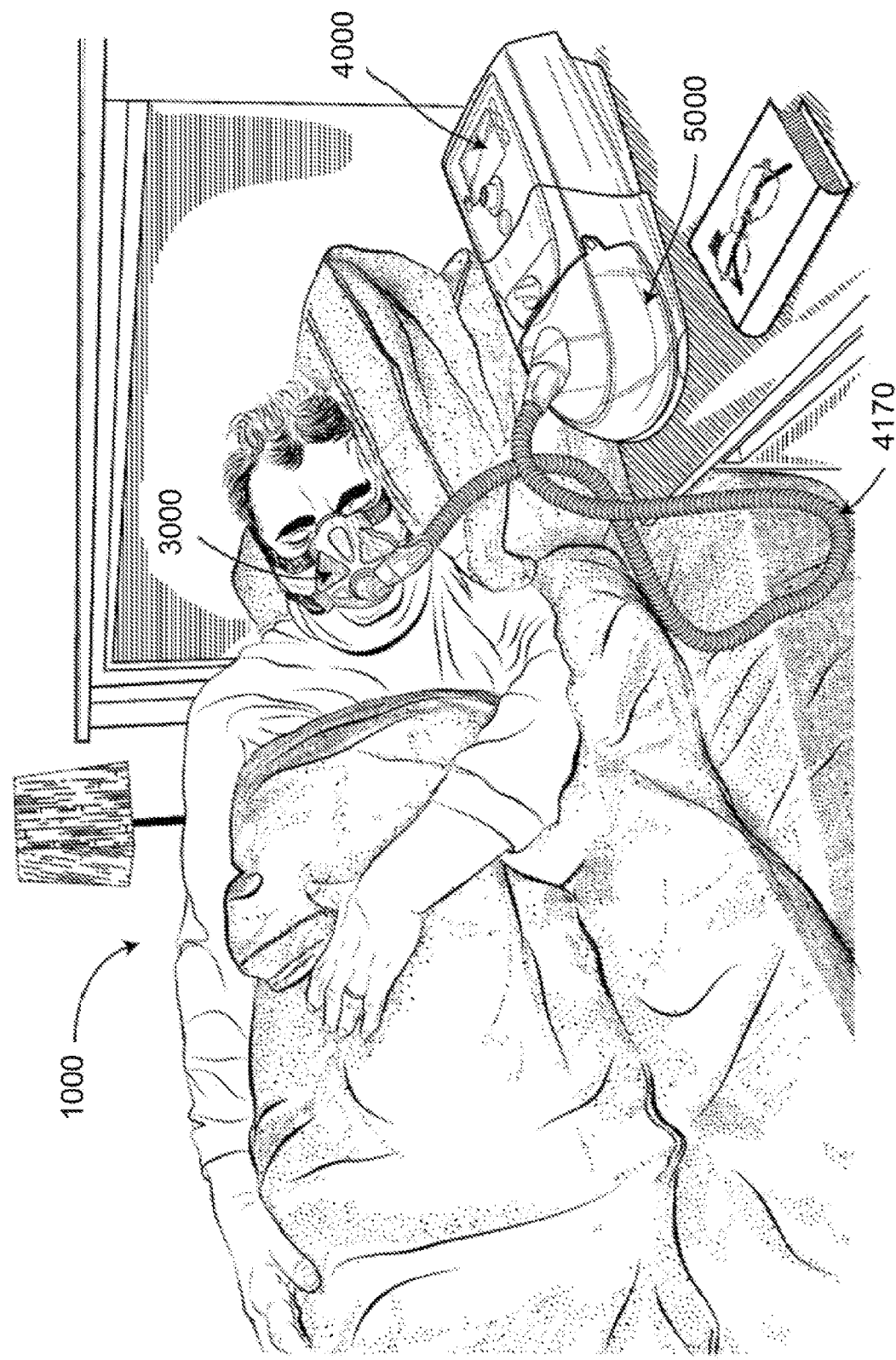
FIG. 1c shows a PAP device in use on a patient with a full-face mask.
Figure 2A:
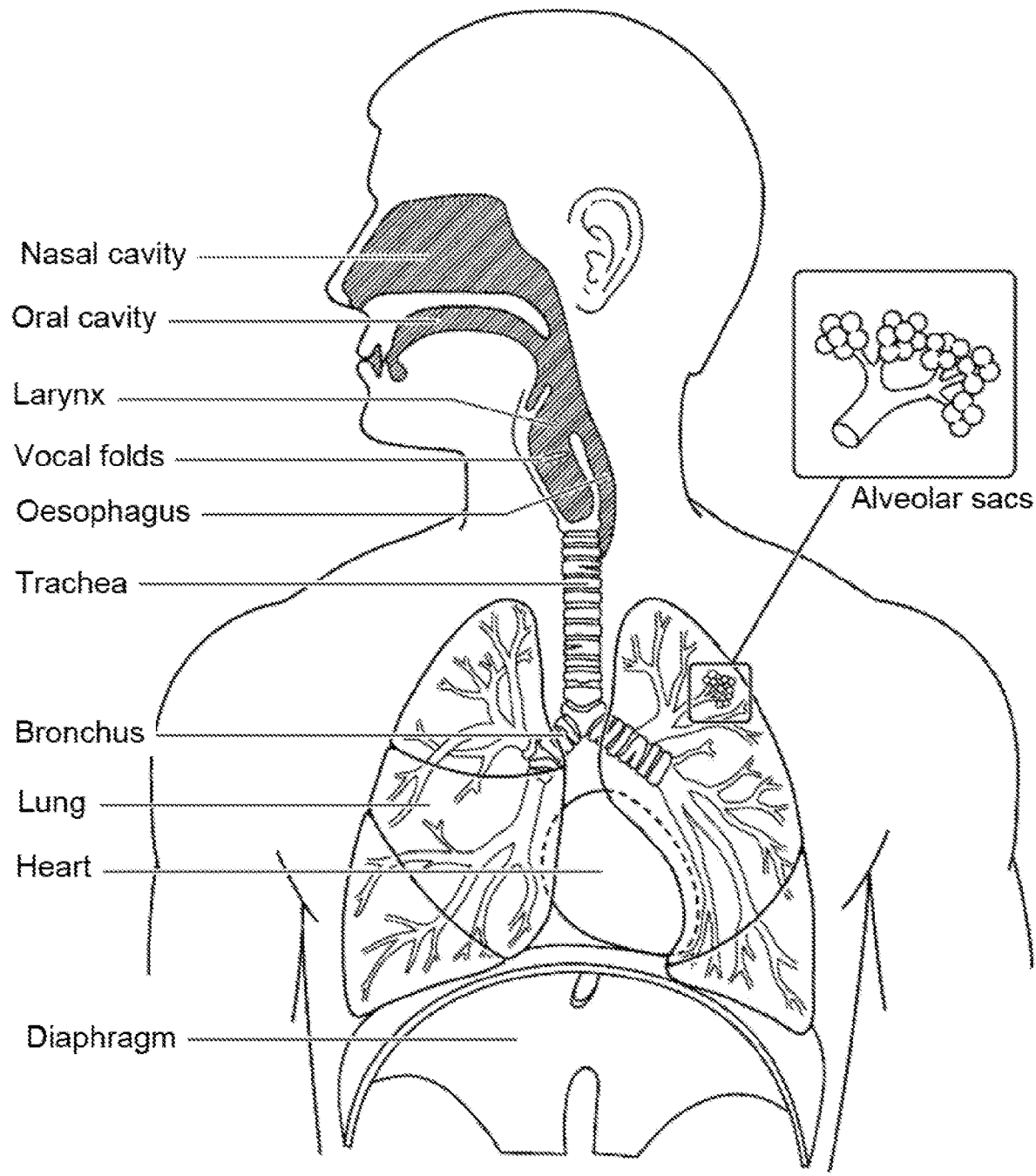

FIG. 2a shows an overview of a human respiratory system including the nasal and oral cavities, the larynx, vocal folds, oesophagus, trachea, bronchus, lung, alveolar sacs, heart and diaphragm.

Figure 2B:
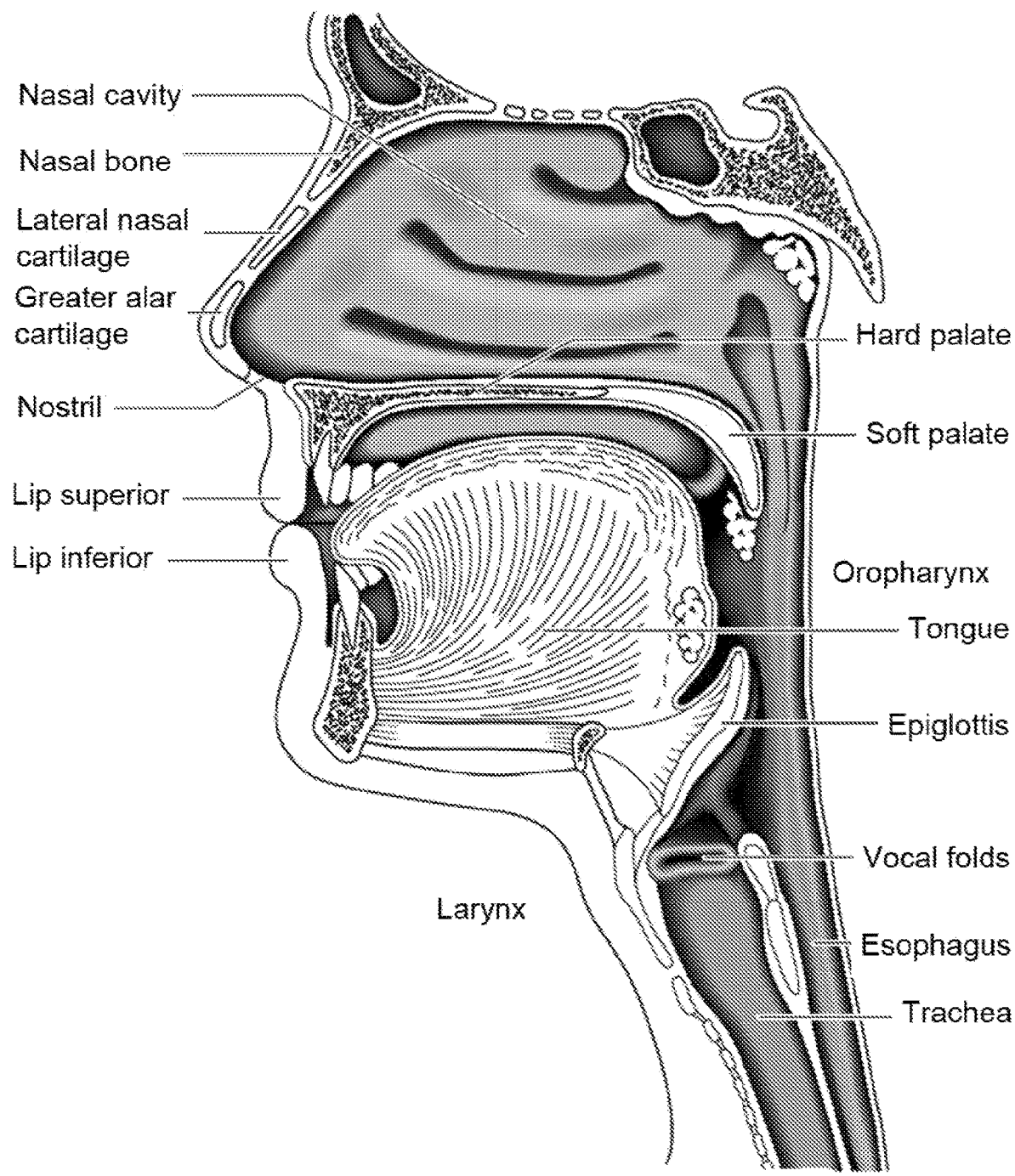

FIG. 2b shows a view of a human upper airway including the nasal cavity, nasal bone, lateral nasal cartilage, greater alar cartilage, nostril, lip superior, lip inferior, larynx, hard palate, soft palate, oropharynx, tongue, epiglottis, vocal folds, oesophagus and trachea.

Patient Interface

Figure 3:
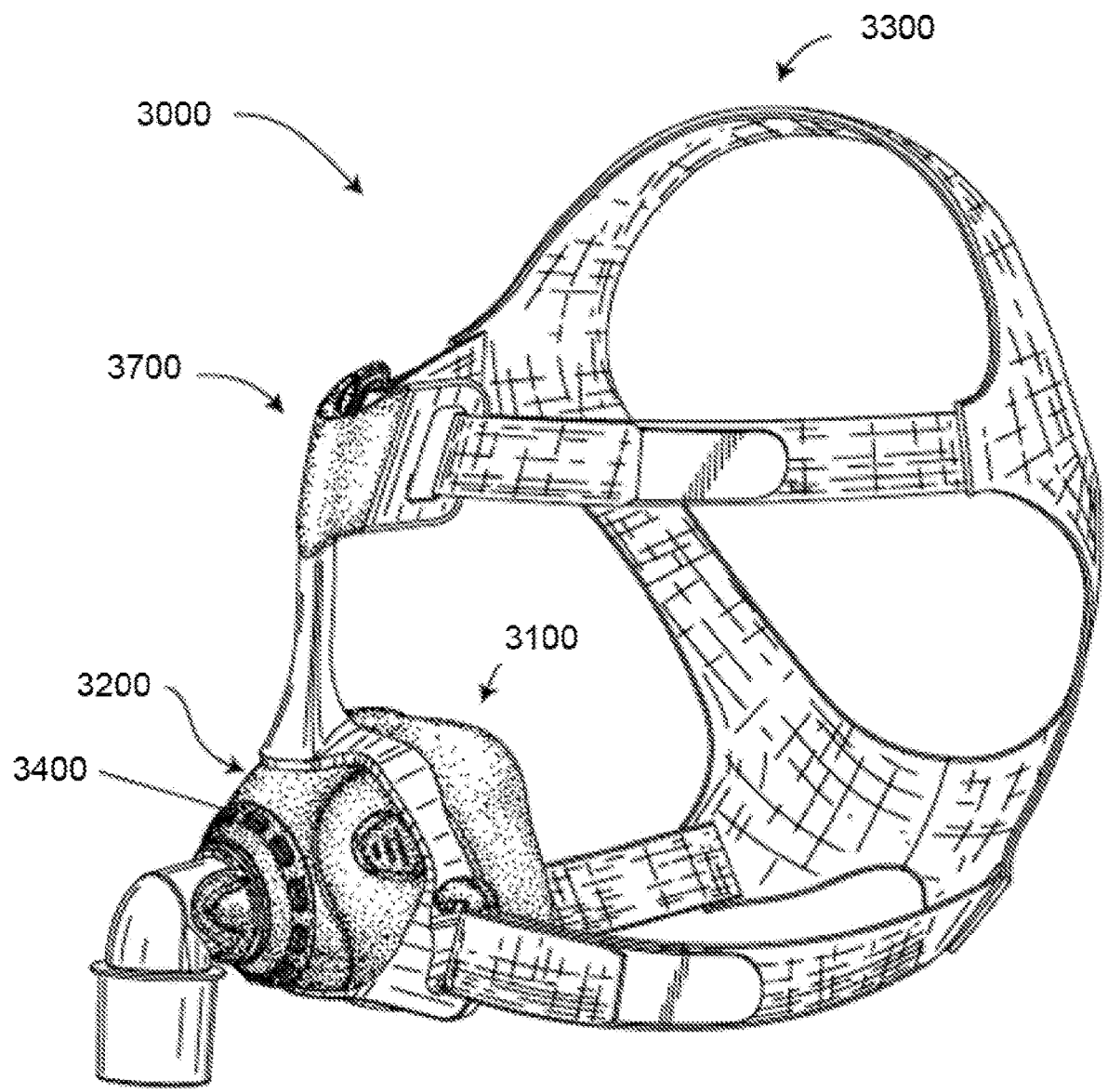

FIG. 3 shows a patient interface in accordance with one form of the present technology.

Pap Device

Figure 4A:
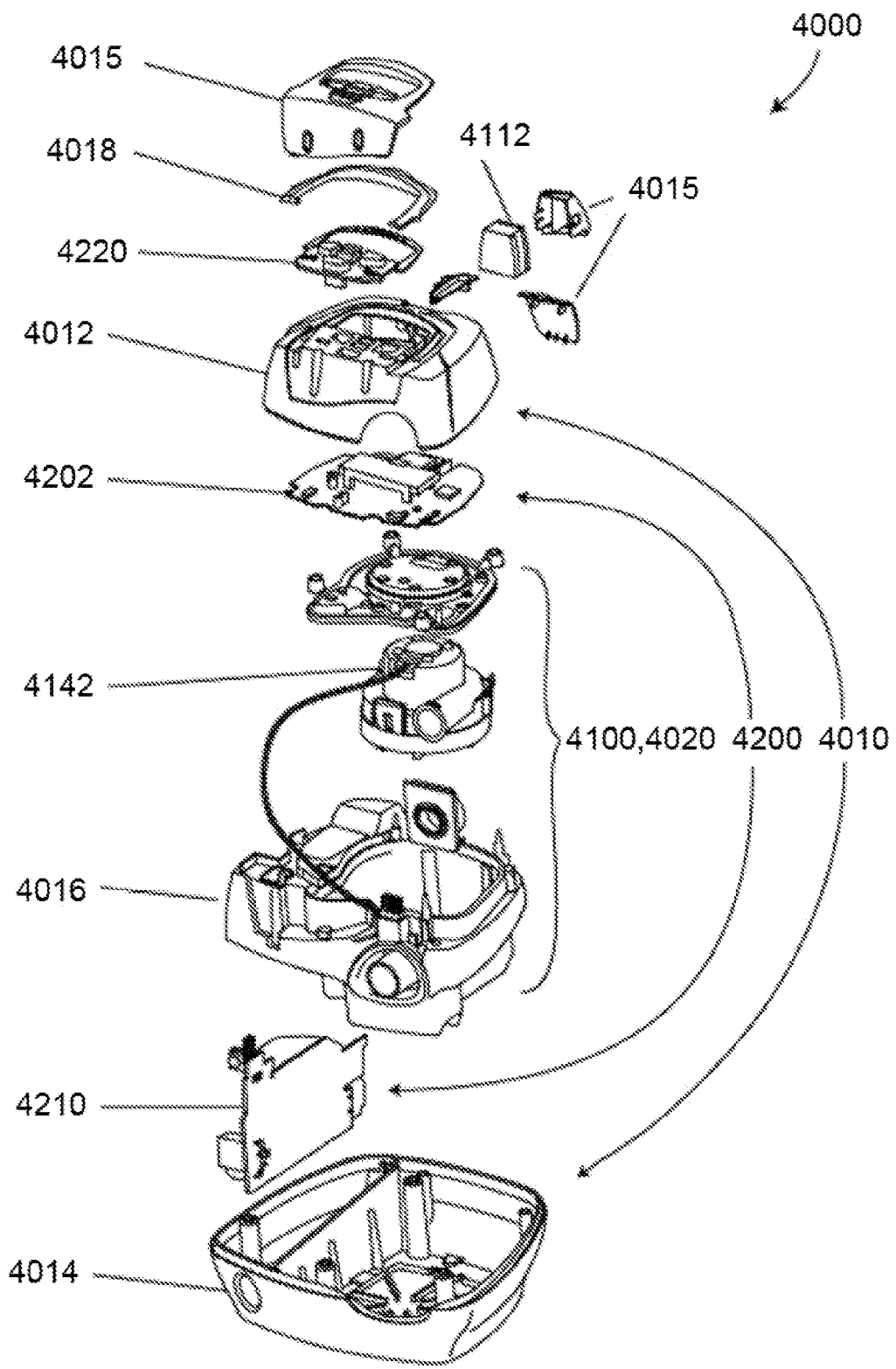

FIG. 4a shows an example PAP device in accordance with one form of the present technology.

Figure 4B:
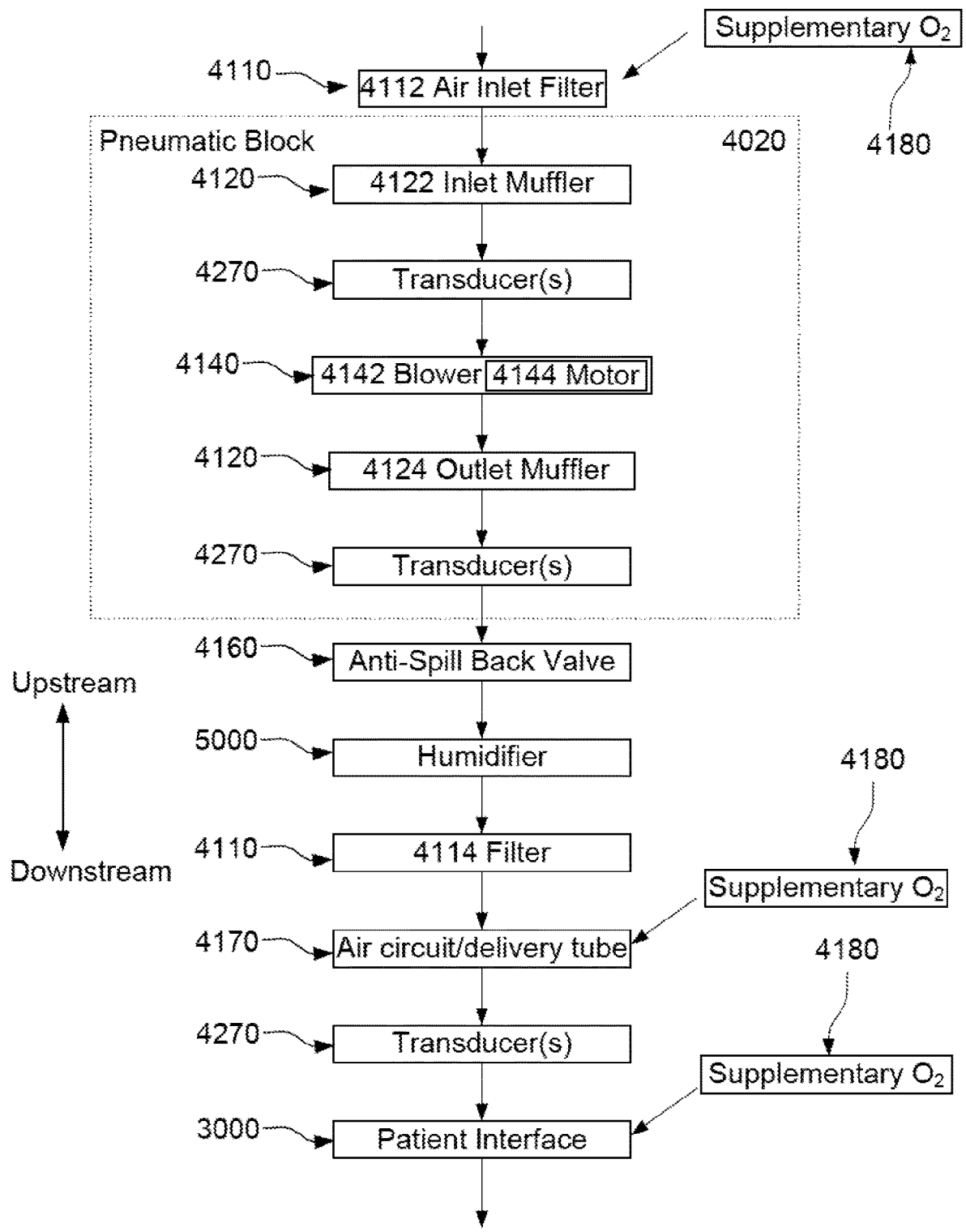

FIG. 4b shows a schematic diagram of an example pneumatic circuit of a PAP device. The directions of upstream and downstream are indicated.

Figure 4C:
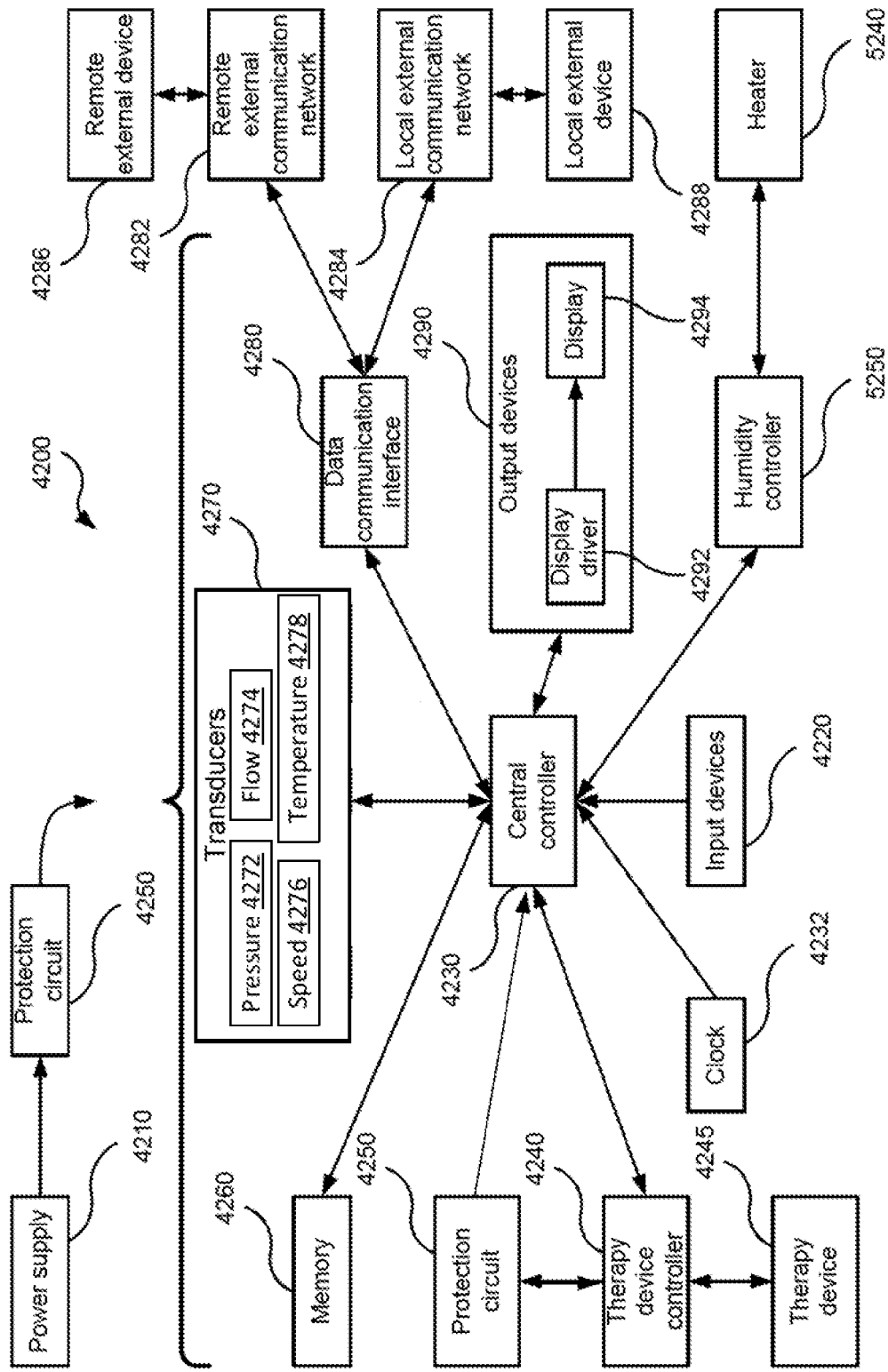

FIG. 4c shows a schematic diagram of some example electrical components of a PAP device.

Figure 4D:
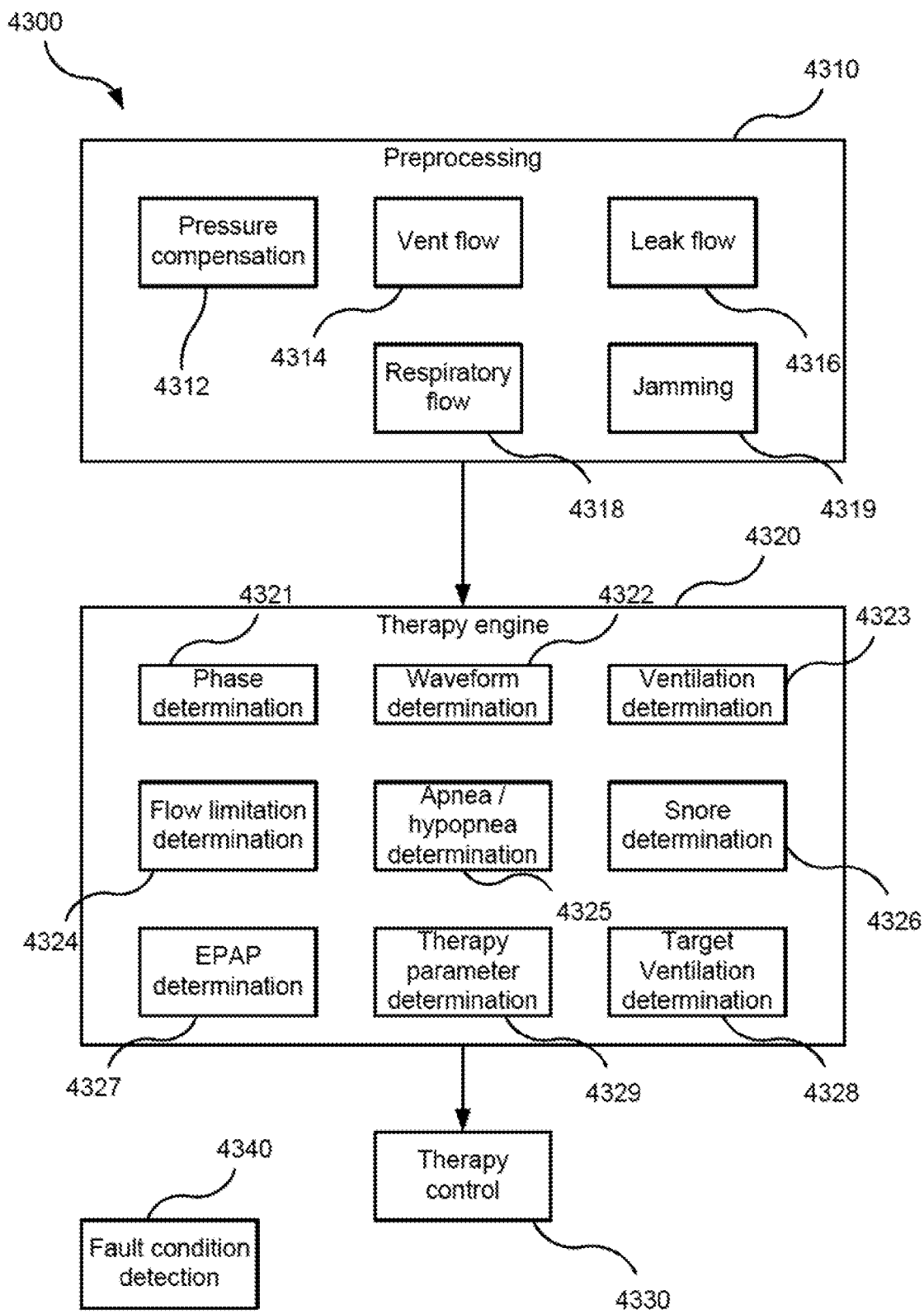

FIG. 4d shows a schematic diagram of example processes (e.g, algorithms) that may be implemented in processor or central controller of a PAP device of the present technology. In this figure, arrows with solid lines indicate an actual flow of information, for example via an electronic signal.

Humidifier

Figure 5:
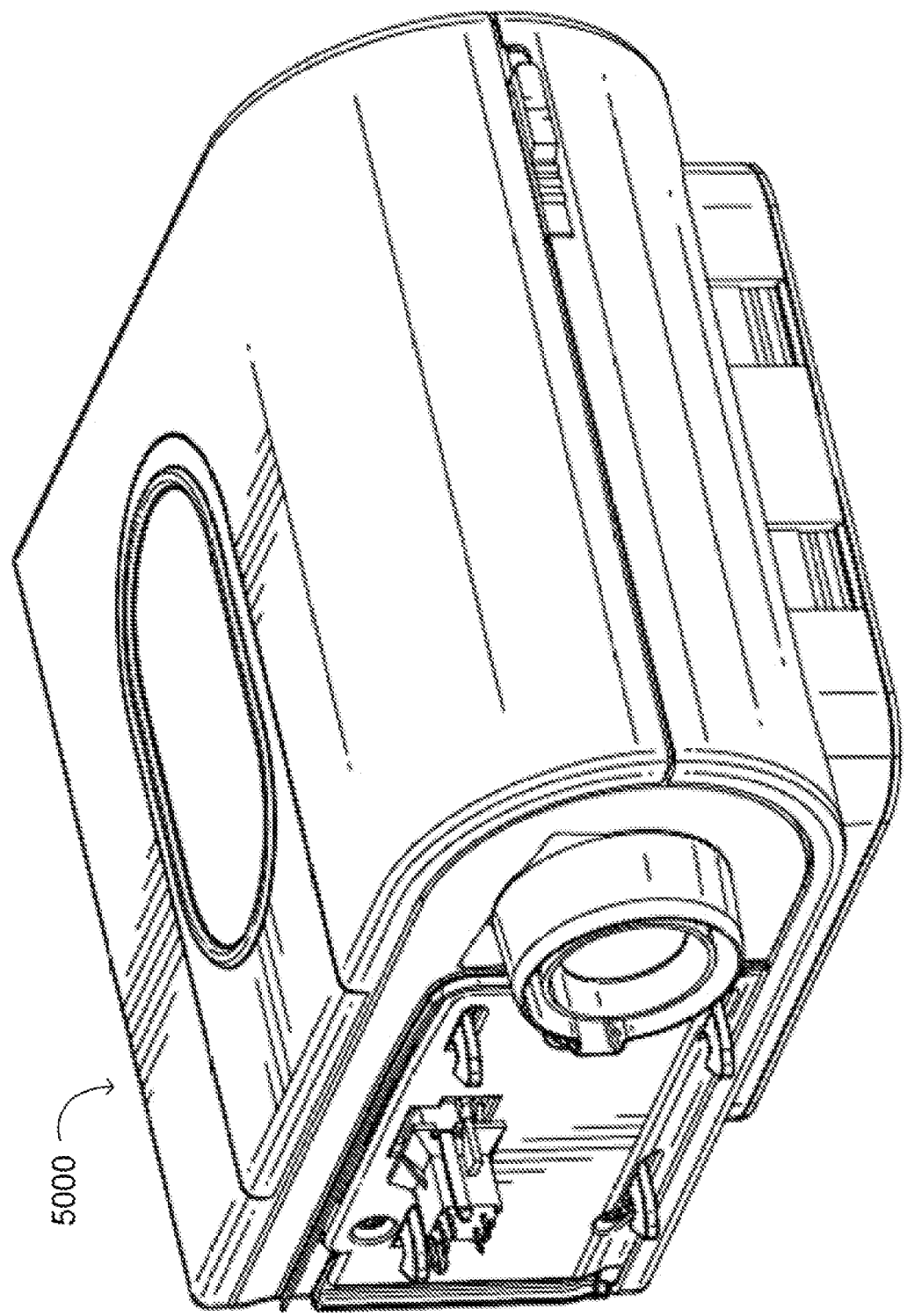

FIG. 5 shows a humidifier in accordance with one aspect of the present technology.

Example Protection Components

Figure 6:
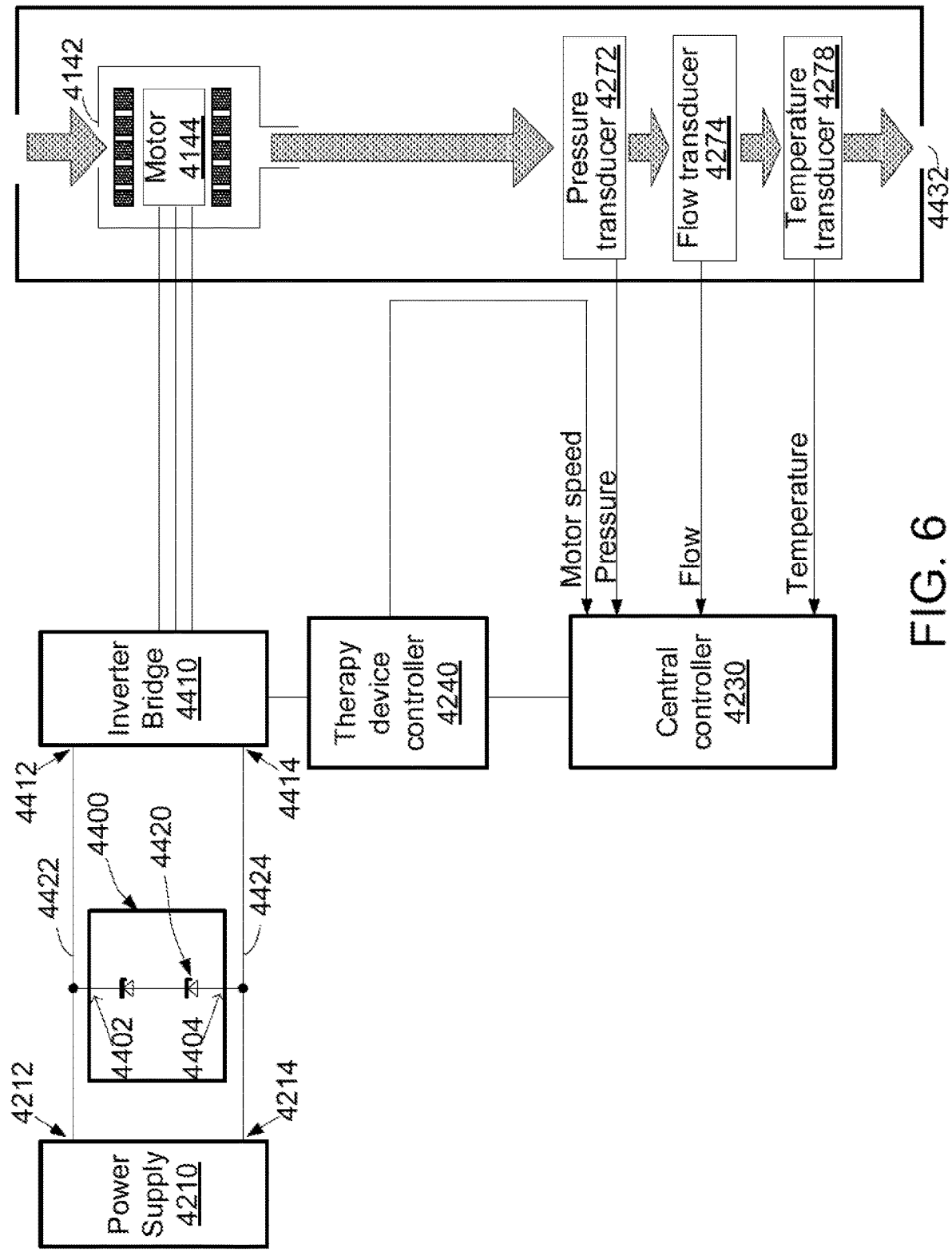

FIG. 6 is a schematic diagram of aspects of a PAP device showing a transient absorption diode circuit implemented therein in accordance with one aspect of the present technology.

Figure 7:
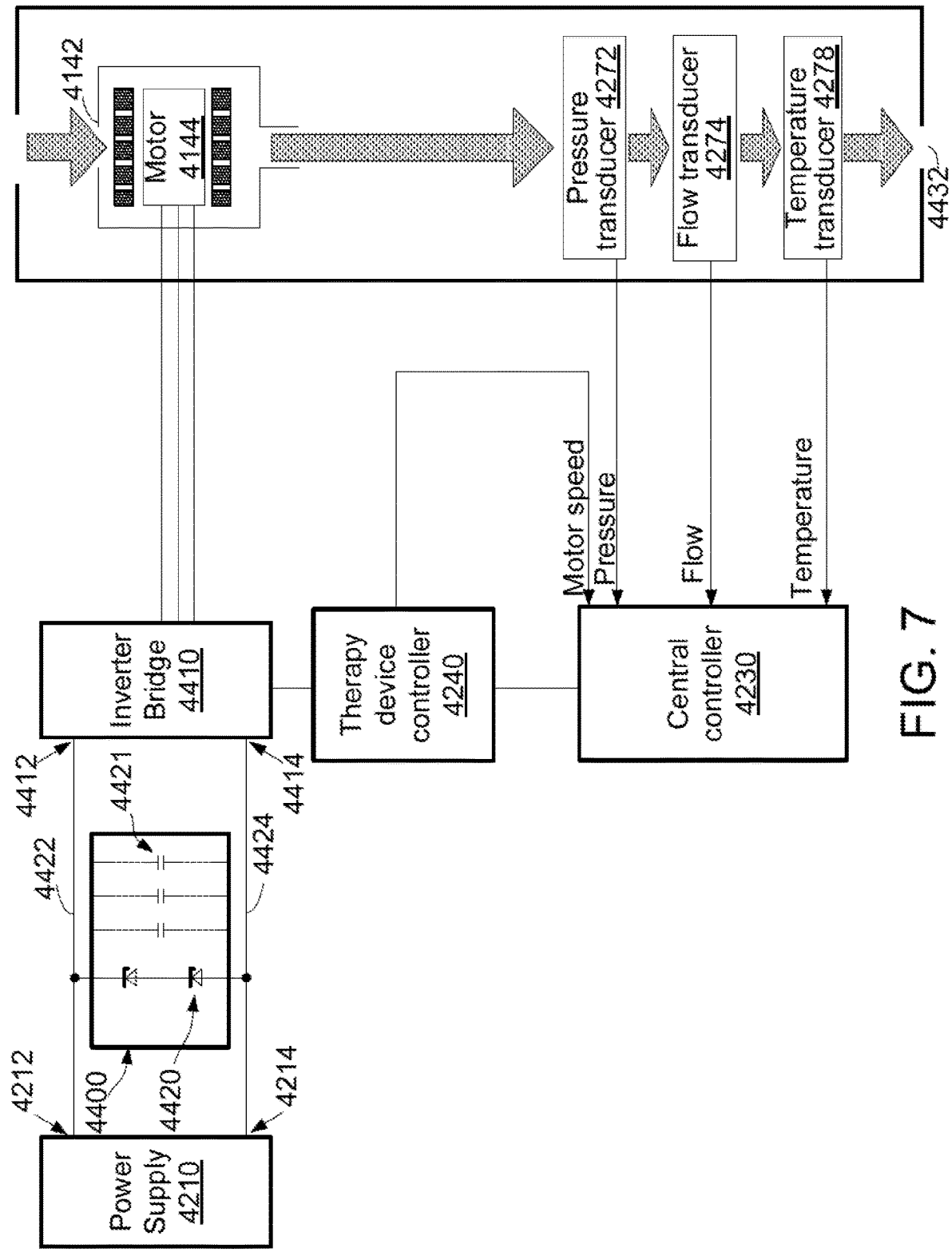

FIG. 7 is a schematic diagram of aspects of a PAP device showing a transient absorption diode circuit implemented therein in accordance with another aspect of the present technology.

Figure 8:
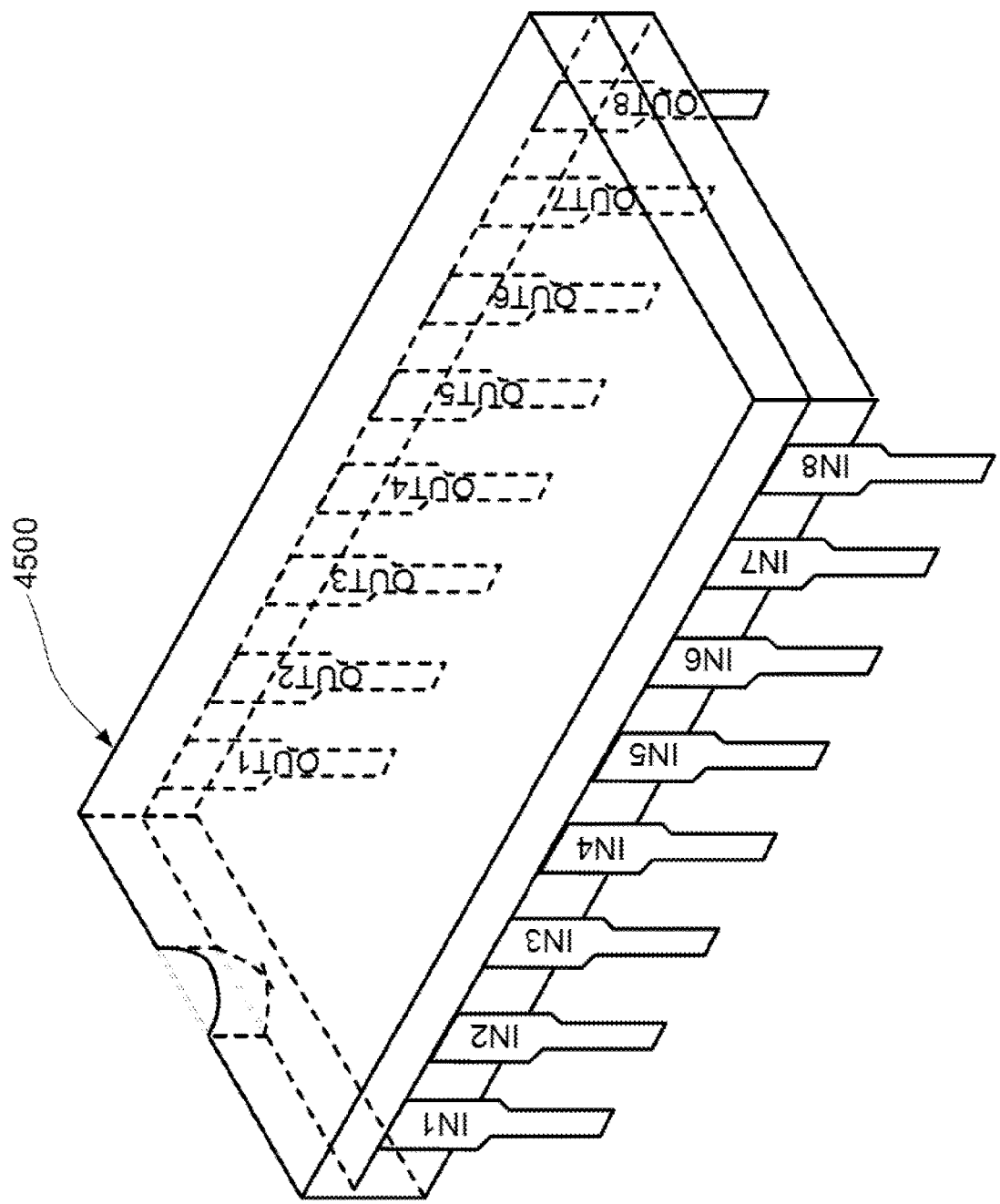

FIG. 8 shows a perspective view of an example fault mitigation integrated circuit in accordance with one aspect of the present technology.

Figure 9:
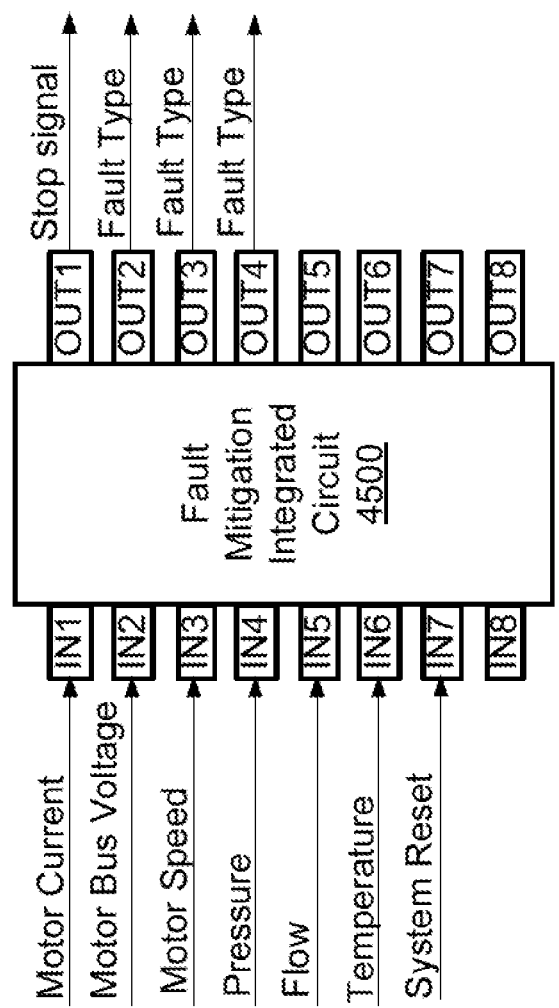

FIG. 9 is a plan view of a fault mitigation integrated circuit of FIG. 8 showing input and output terminals of the circuit.

Figure 10:
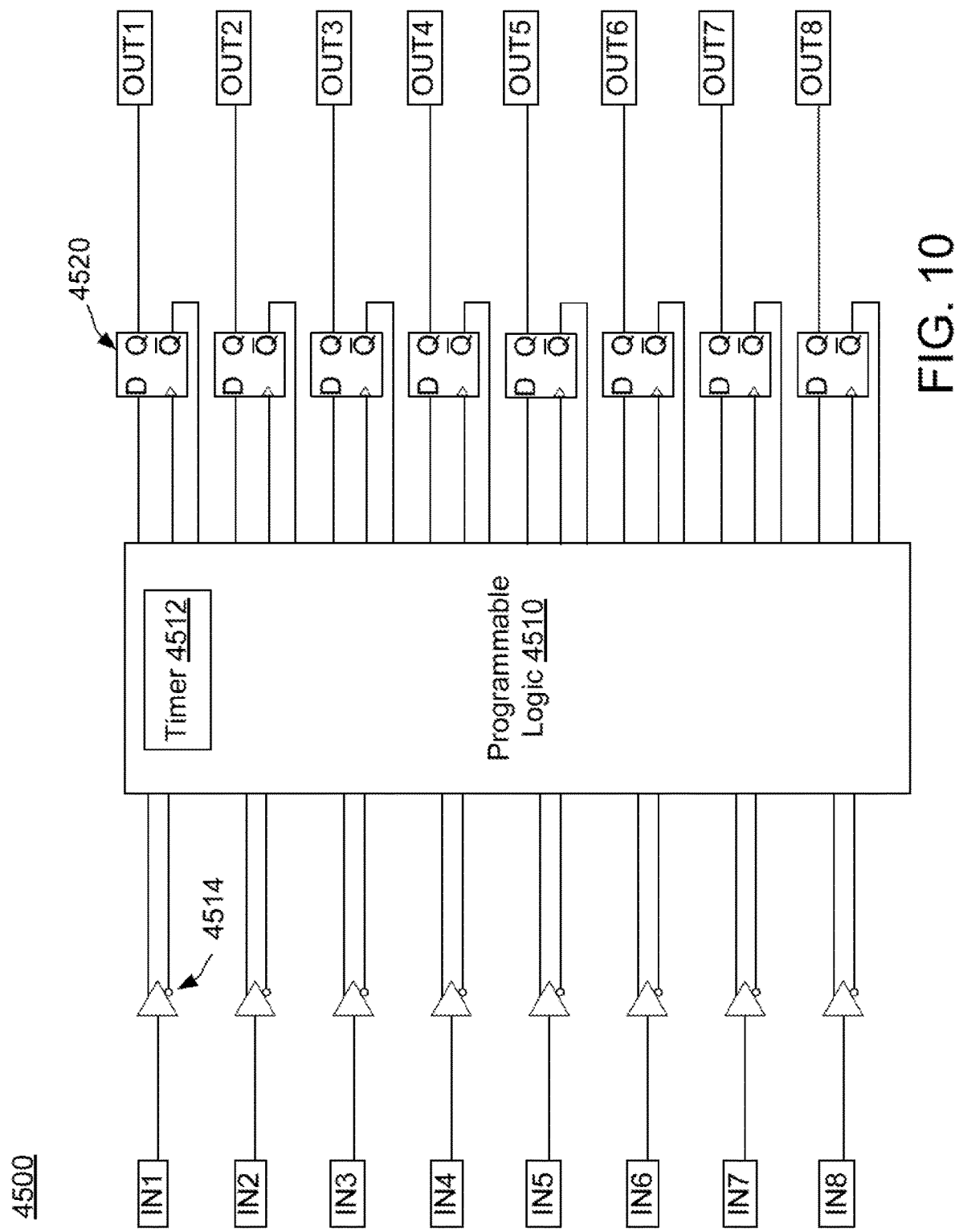

FIG. 10 is a diagram illustrating example elements of a fault mitigation integrated circuit such as the version of FIG. 8.

Figure 11:
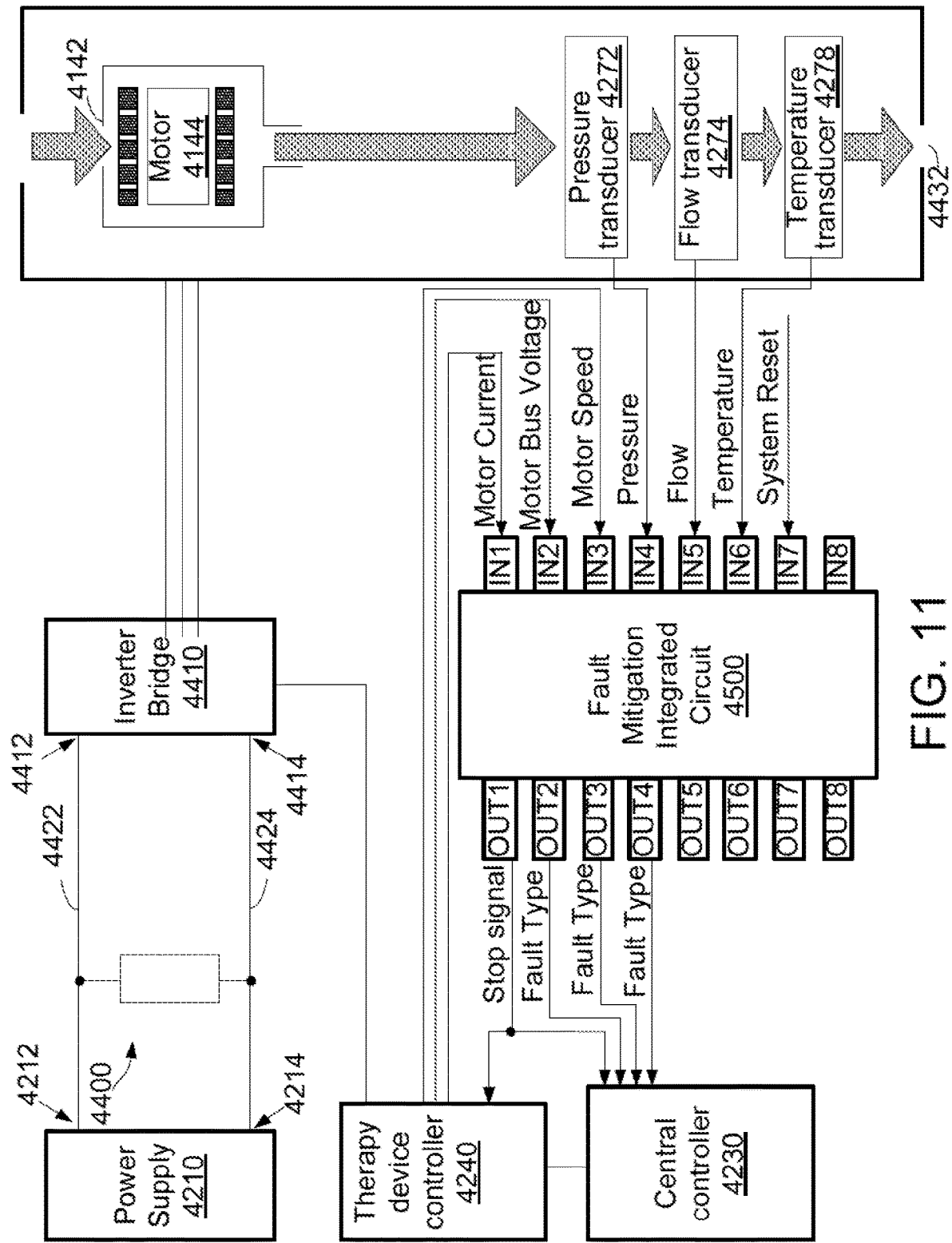

FIG. 11 is a schematic diagram illustrating aspects of a PAP device with a fault mitigation integrated circuit implemented therein.

FIG. 12 is an example list of fault types in association with the signal output of output terminals or pins of a circuit such as the circuit of FIG. 8 or 9.

DETAILED DESCRIPTION OF EXAMPLES OF THE TECHNOLOGY

Before the present technology is described in further detail, it is to be understood that the technology is not limited to the particular examples described herein, which may vary. It is also to be understood that the terminology used in this disclosure is for the purpose of describing only the particular examples discussed herein, and is not intended to be limiting.

Treatment Systems

In one form, the present technology comprises apparatus for treating a respiratory disorder. The apparatus may comprise a flow generator or blower for supplying pressurised respiratory gas, such as air, to the patient 1000 via an air delivery tube leading to a patient interface 3000.

Therapy

In one form, the present technology comprises a method for treating a respiratory disorder comprising the step of applying positive pressure to the entrance of the airways of a patient 1000.

Nasal CPAP for OSA

In one form, the present technology comprises a method of treating Obstructive Sleep Apnea in a patient by applying nasal continuous positive airway pressure to the patient.

In certain embodiments of the present technology, a supply of air at positive pressure is provided to the nasal passages of the patient via one or both nares.

Patient Interface 3000

With reference to FIG. 3, a non-invasive patient interface 3000 in accordance with one aspect of the present technology comprises the following functional aspects: a seal-forming structure 3100, a plenum chamber 3200, a positioning and stabilising structure 3300 and a connection port for connection to air circuit 4170. In some forms a functional aspect may be provided by one or more physical components. In some forms, one physical component may provide one or more functional aspects. In use the seal-forming structure 3100 is arranged to surround an entrance to the airways of the patient so as to facilitate the supply of air at positive pressure to the airways. The patient interface 3000 may include a vent 3400 constructed and arranged to allow for the washout of exhaled carbon dioxide. The patient interface 3000 may include a forehead support 3700. Other types of patient interface may also be implemented.

PAP Device 4000

With reference to FIG. 4a, a respiratory treatment apparatus such as a PAP device 4000 may include mechanical and pneumatic components 4100, electrical components 4200 and may be programmed to execute one or more algorithms 4300 (shown in FIG. 4d). As illustrated in the version of FIG. 4a, the PAP device has an external housing 4010 formed in two parts, an upper portion 4012 of the external housing 4010, and a lower portion 4014 of the external housing 4010. In alternative forms, the external housing 4010 may include one or more panel(s) 4015. The PAP device 4000 comprises a chassis 4016 that supports one or more internal components of the PAP device 4000. In one form a pneumatic block 4020 is supported by, or formed as part of the chassis 4016. The PAP device 4000 may include a handle 4018.

Referring to FIG. 4b, the pneumatic path of the PAP device 4000 comprises an inlet air filter 4112, an inlet muffler 4122, a controllable pressure device 4140 capable of supplying air at positive pressure (preferably a blower 4142), and an outlet muffler 4124. One or more pressure sensors and flow sensors are included in the pneumatic path.

The pneumatic block 4020 may include a portion of the pneumatic path that is located within the external housing 4010.

With reference to FIG. 4c, electronic components 4200 of the PAP device 4000 may include an electrical power supply 4210, one or more input devices 4220, a central controller 4230, a therapy device controller 4240, a therapy device 4245, one or more protection circuits 4250, memory 4260, transducers 4270, data communication interface 4280 and one or more output devices 4290. Electrical components 4200 may be mounted on a single Printed Circuit Board Assembly (PCBA) 4202 as illustrated in FIG. 4a. In an alternative form, the PAP device 4000 may include more than one PCBA 4202.

Referring to FIG. 4d, the central controller 4230 of the PAP device 4000 is programmed to execute one or more algorithm 4300 modules, including in one implementation a pre-processing module 4310, a therapy engine module 4320, a pressure control module 4330, and a fault condition detection module 4340.

According to some aspects of the present technology, the central controller 4230 may optionally omit the fault condition action module 4340. Rather, fault detection may be performed by a fault mitigation integrated circuit 4500 separate from the central controller 4230. Such a fault mitigation integrated circuit 4500 is described in more detail herein.

In one form, the PAP device 4000 may be referred to interchangeably as a ventilator.

PAP Device Mechanical & Pneumatic Components 4100

Air Filter(s) 4110

With reference to FIG. 4b, a PAP device in accordance with one form of the present technology may include an air filter 4110, or a plurality of air filters 4110.

In one form, an inlet air filter 4112 is located at the beginning of the pneumatic path upstream of a blower 4142. See FIG. 4b.

In one form, an outlet air filter 4114, for example an antibacterial filter, is located between an outlet of the pneumatic block 4020 and a patient interface 3000. See FIG. 4b.

Muffler(s) 4120

In one form of the present technology, an inlet muffler 4122 is located in the pneumatic path upstream of a blower 4142. See FIG. 4b.

In one form of the present technology, an outlet muffler 4124 is located in the pneumatic path between the blower 4142 and a patient interface 3000. See FIG. 4b.

Pressure Device 4140

With reference to FIG. 4b, in one form of the present technology, a pressure device 4140 for producing a flow of air at positive pressure is a controllable blower 4142. For example, the blower may include a brushless DC electric motor 4144 with one or more impellers housed in a volute. The blower is capable of delivering a supply of air, for example about 120 litres/minute, at a positive pressure in a range from about 4 cmH$_2$O to about 20 cmH$_2$O, or in other forms up to about 30 cmH$_2$O.

The pressure device 4140 is under the control of the therapy device controller 4240.

Transducer(s) 4270

With continued reference to FIG. 4b, in one form of the present technology, one or more transducers 4270 are located upstream of the pressure device 4140. The one or more transducers 4270 are constructed and arranged to measure properties of the air at that point in the pneumatic path.

In one form of the present technology, one or more transducers 4270 are located downstream of the pressure device 4140, and upstream of the air circuit 4170. The one or more transducers 4270 are constructed and arranged to measure properties of the air at that point in the pneumatic path.

In one form of the present technology, one or more transducers 4270 are located proximate to the patient interface 3000.

Anti-Spill Back Valve 4160

In one form of the present technology, an anti-spill back valve is located between the humidifier 5000 and the pneumatic block 4020. The anti-spill back valve is constructed and arranged to reduce the risk that water will flow upstream from the humidifier 5000, for example to the motor 4144.

Air Circuit 4170

As shown in FIG. 4b, an air circuit 4170 in accordance with an aspect of the present technology is constructed and arranged to allow a flow of air or breathable gasses between the pneumatic block 4020 and the patient interface 3000.

Oxygen Delivery

With continued reference to FIG. 4b, in one form of the present technology, supplemental oxygen 4180 is delivered to a point in the pneumatic path.

In one form of the present technology, supplemental oxygen 4180 is delivered upstream of the pneumatic block 4020.

In one form of the present technology, supplemental oxygen 4180 is delivered to the air circuit 4170.

In one form of the present technology, supplemental oxygen 4180 is delivered to the patient interface 3000.

PAP Device Electrical Components 4200

Basic PAP Device

Power Supply 4210

Referring to FIG. 4c, power supply 4210 supplies power to the other components of the basic PAP device 4000: the input device 4220, the central controller 4230, the therapy device 4245, and the output device 4290.

In one form of the present technology, power supply 4210 is internal of the external housing 4010 of the PAP device 4000. In another form of the present technology, power supply 4210 is external of the external housing 4010 of the PAP device 4000.

The power supply 4210 may include a Mains powered switched-mode power supply, which may block negative regenerative currents.

Input Device(s) 4220

Input devices 4220 (shown in FIG. 4c) may include one or more of buttons, switches or dials to allow a person to interact with the PAP device 4000. The buttons, switches or dials may be physical devices, or software devices accessible via a touch screen. The buttons, switches or dials may, in one form, be physically connected to the external housing 4010, or may, in another form, be in wireless communication with a receiver that is in electrical connection to the central controller 4230.

In one form the input device 4220 may be constructed and arranged to allow a person to select a value and/or a menu option.

Central Controller 4230

In one form of the present technology, a central controller 4230 (shown in FIG. 4c) is a dedicated electronic circuit configured to receive input signal(s) from the input device 4220, and to provide output signal(s) to the output device 4290 and/or the therapy device controller 4240.

In one form, the central controller 4230 is an application-specific integrated circuit. In another form, the central controller 4230 may be formed with discrete electronic components.

Therapy Device 4245

In one form of the present technology, the therapy device 4245 (shown in FIG. 4c) is configured to deliver therapy to a patient 1000 under the control of the central controller 4230. The therapy device 4245 may be the controllable pressure device 4140, such as a positive air pressure device 4140.

Output Device 4290

An output device 4290 (shown in FIG. 4c) in accordance with the present technology may take the form of one or more of a visual, audio, and haptic output. A visual output may be a Liquid Crystal Display (LCD) or Light Emitting Diode (LED) display. An audio output may be a speaker or audio tone emitter.

Microprocessor-Controlled PAP Device

Power Supply 4210

In one form of the present technology power supply 4210 (shown in FIG. 4c) is internal of the external housing 4010 of the PAP device 4000. In another form of the present technology, power supply 4210 is external of the external housing 4010 of the PAP device 4000.

In one form of the present technology power supply 4210 provides electrical power to the PAP device 4000 only. In another form of the present technology, power supply 4210 provides electrical power to both PAP device 4000 and humidifier 5000.

Input Devices 4220

In one form of the present technology, a PAP device 4000 includes one or more input devices 4220 (shown in FIG. 4c) in the form of buttons, switches or dials to allow a person to interact with the device. The buttons, switches or dials may be physical devices, or software devices accessible via a touch screen. The buttons, switches or dials may, in one form, be physically connected to the external housing 4010, or may, in another form, be in wireless communication with a receiver that is in electrical connection to the central controller 4230.

In one form the input device 4220 may be constructed and arranged to allow a person to select a value and/or a menu option.

Central Controller 4230

In one form of the present technology, the central controller 4230 (shown in FIG. 4c) may be a processor or a microprocessor, suitable to control a PAP device 4000 such as an x86 INTEL processor.

The central controller 4230 suitable to control a PAP device 4000 in accordance with another form of the present technology includes a processor based on ARM Cortex-M processor from ARM Holdings. For example, an STM32 series microcontroller from ST MICROELECTRONICS may be used.

In a further alternative form of the present technology, the central controller 4230 may include a member selected from the family ARMS-based 32-bit RISC CPUs. For example, an STR9 series microcontroller from ST MICROELECTRONICS may be used.

In certain alternative forms of the present technology, a 16-bit RISC CPU may be used as the central controller 4230 for the PAP device 4000. For example, a processor from the MSP430 family of microcontrollers, manufactured by TEXAS INSTRUMENTS, may be used.

The central controller 4230 is configured to receive input signal(s) from one or more transducers 4270, and one or more input devices 4220.

The central controller 4230 is configured to provide output signal(s) to one or more of an output device 4290, a therapy device controller 4240, a data communication interface 4280 and humidifier controller 5250.

The central controller 4230, or multiple such processors, is configured to implement the one or more methodologies described herein such as the one or more algorithms 4300 (shown in FIG. 4d) expressed as computer programs stored in a computer readable storage medium, such as memory 4260. In some cases, as previously discussed, such processor(s) may be integrated with a PAP device 4000. However, in some devices the processor(s) may be implemented discretely from the flow generation components of the PAP device, such as for purpose of performing any of the methodologies described herein without directly controlling delivery of a respiratory treatment. For example, such a processor may perform any of the methodologies described herein for purposes of determining control settings for a ventilator or other respiratory related events by analysis of stored data such as from any of the sensors described herein.

Clock 4232

Preferably PAP device 4000 includes a clock 4232 (shown in FIG. 4c) that is connected to processor or central controller 4230.

Therapy Device Controller 4240

In one form of the present technology, therapy device controller 4240 (shown in FIG. 4c) is a therapy control module 4330 (shown in FIG. 4d) that may implement features of the algorithms 4300 executed by or in conjunction with the central controller 4230. In some cases, the therapy device controller 4240 may be implemented with a motor drive.

In one form of the present technology, therapy device controller 4240 is a dedicated motor control integrated circuit. For example, in one form a MC33035 brushless DC motor controller, manufactured by ONSEMI is used.

Protection Circuits 4250

Preferably a PAP device 4000 in accordance with the present technology includes one or more protection circuits 4250 such as shown in FIG. 4c.

One form of protection circuit 4250 in accordance with the present technology is an electrical protection circuit.

One form of protection circuit 4250 in accordance with the present technology is a temperature or pressure safety circuit.

In some versions of the present technology, a protection circuit 4250 may include a transient absorption diode circuit 4400. The circuit may be configured to absorb energy generated or converted from rotational kinetic energy, such as from the blower motor. According to another aspect of the present technology, a protection circuit 4250 may include a fault mitigation integrated circuit 4500 (such as the single IC circuit that is shown in FIGS. 8-9). Specific embodiments of the transient absorption diode circuit 4400 and the fault mitigation integrated circuit 4500 are discussed in more detail herein.

Memory 4260

In accordance with one form of the present technology the PAP device 4000 includes memory 4260 (shown in FIG. 4c), preferably non-volatile memory. In some forms, memory 4260 may include battery powered static RAM. In some forms, memory 4260 may include volatile RAM.

Preferably memory 4260 is located on PCBA 4202 (shown in FIG. 4a). Memory 4260 may be in the form of EEPROM, or NAND flash.

Additionally or alternatively, PAP device 4000 includes removable form of memory 4260, for example a memory card made in accordance with the Secure Digital (SD) standard.

In one form of the present technology, the memory 4260 acts as a computer readable storage medium on which is stored computer program instructions expressing the one or more methodologies described herein, such as the one or more algorithms 4300.

Transducers 4270

Transducers 4270 (shown in FIG. 4c) may be internal to the device, or external to the PAP device. External transducers may be located for example on or form part of the air delivery circuit, and/or the patient interface. External transducers may be in the form of non-contact sensors such as a Doppler radar movement sensor that transmit or transfer data to the PAP device.

Flow

A flow transducer 4274 (shown in FIG. 4c) in accordance with the present technology may be based on a differential pressure transducer, for example, an SDP600 Series differential pressure transducer from SENSIRION. The differential pressure transducer is in fluid communication with the pneumatic circuit, with one of each of the pressure transducers connected to respective first and second points in a flow restricting element.

In use, a signal representing total flow Qt from the flow transducer 4274 is received by the central controller 4230. However, other sensors for producing such a flow signal or estimating flow may be implemented. For example, a mass flow sensor, such as a hot wire mass flow sensor, may be implemented to generate a flow signal in some embodiments. Optionally, flow may be estimated from one or more signals of other sensors described here, such as in accordance with any of the methodologies described in a U.S. patent application Ser. No. 12/192,247, the disclosure of which is incorporated herein by reference.

Pressure

A pressure transducer 4272 (shown in FIG. 4*c*) in accordance with the present technology is located in fluid communication with the pneumatic circuit. An example of a suitable pressure transducer is a sensor from the HONEYWELL ASDX series. An alternative suitable pressure transducer is a sensor from the NPA Series from GENERAL ELECTRIC.

In use, a signal from the pressure transducer 4272 is received by the central controller 4230. In one form, the signal from the pressure transducer 4272 is filtered prior to being received by the central controller 4230.

Motor Speed

In one form of the present technology a motor speed signal from a motor speed transducer 4276 (shown in FIG. 4*c*) is generated. A motor speed signal is preferably provided by therapy device controller 4240. Motor speed may, for example, be generated by a speed sensor, such as a Hall Effect sensor.

Temperature

The temperature transducer 4278 (shown in FIG. 4*c*) may measure temperature of the gas in the pneumatic circuit. One example of the temperature transducer 4278 is a thermocouple or a resistance temperature detector (RTD).

Data Communication Systems

In one preferred form of the present technology, a data communication interface 4280 (shown in FIG. 4*c*) is provided, and is connected to the central controller 4230. Data communication interface 4280 is preferably connectable to remote external communication network 4282. Data communication interface 4280 is preferably connectable to local external communication network 4284. Preferably remote external communication network 4282 is connectable to remote external device 4286. Preferably local external communication network 4284 is connectable to local external device 4288.

In one form, data communication interface 4280 is part of the central controller 4230. In another form, data communication interface 4280 is an integrated circuit that is separate from the central controller 4230.

In one form, remote external communication network 4282 is the Internet. The data communication interface 4280 may use wired communication (e.g. via Ethernet, or optical fibre) or a wireless protocol to connect to the Internet.

In one form, local external communication network 4284 utilises one or more communication standards, such as Bluetooth, or a consumer infrared protocol.

In one form, remote external device 4286 is one or more computers, for example a cluster of networked computers. In one form, remote external device 4286 may be virtual computers, rather than physical computers. In either case, such remote external device 4286 may be accessible to an appropriately authorised person such as a clinician.

Preferably local external device 4288 is a personal computer, mobile phone, tablet or remote control.

Output Devices Including Optional Display, Alarms

An output device 4290 (shown in FIG. 4*c*) in accordance with the present technology may take the form of one or more of a visual, audio and haptic unit. A visual display may be a Liquid Crystal Display (LCD) or Light Emitting Diode (LED) display.

Display Driver 4292

A display driver 4292 (shown in FIG. 4*c*) receives as an input the characters, symbols, or images intended for display on the display 4294, and converts them to commands that cause the display 4294 to display those characters, symbols, or images.

Display 4294

A display 4294 (shown in FIG. 4*c*) is configured to visually display characters, symbols, or images in response to commands received from the display driver 4292. For example, the display 4294 may be an eight-segment display, in which case the display driver 4292 converts each character or symbol, such as the figure "0", to eight logical signals indicating whether the eight respective segments are to be activated to display a particular character or symbol.

Transient Absorption Diode Circuit 4400

According to some aspects of the present technology, a protection circuit 4250 may include a kinetic energy absorption circuit to absorb excess energy, e.g., voltage and/or current, that occurs during braking or sudden deceleration of the motor 4144. Such energy may be generated, or regenerated, by the rotational kinetic energy of the motor during braking or sudden deceleration.

By way of example, when the PAP device is in a normal steady state, the motor 4144 may operate at a certain speed. In this state, the motor 4144 may consume power provided by the power supply 4210 in proportion to the load applied and the internal losses. During this process, the motor 4144 converts the electrical energy, or power, provided by the power supply 4210 into rotational kinetic energy.

When sudden deceleration or braking occurs, the motor 4144 reverses the energy conversion for a transient period of time. For example, when sudden deceleration or braking occurs, the motor 4144 generates energy as a result of the rotational kinetic energy imposed in the opposite direction to the direction of rotation. When sudden deceleration or braking occurs, the motor 4144 converts the rotational kinetic energy into electrical energy. This typically may result in a rapid rise of voltage or current on the bus or circuit lines between the power supply 4210 and the motor 4144. To prevent such a rise of voltage and/or current, a kinetic energy absorption circuit may be placed in the bus or circuit lines between the power supply 4210 and the motor 4144.

In one form, the kinetic energy absorption circuit may be a transient absorption diode circuit 4400 such as in the configuration illustrated in FIG. 6. FIG. 6 is a schematic diagram of aspects of an example PAP device 4000. As shown in FIG. 6, the transient absorption diode circuit 4400 may be implemented between the power supply 4210 and the motor 4144. For example, it may be implemented between the power supply 4210 and a bridge circuit such as an inverter bridge 4410.

The inverter bridge 4410 is an electronic circuit. Such a circuit may permit one or more levels of voltage to be applied across the motor 4144 in either direction to cause acceleration or deceleration of the motor 4144. For example, the inverter bridge 4410 may be implemented with one or more switching elements (e.g., transistors or MOSFETS). The operation of the motor 4144 may be set by controlling the opening or closing of the different switches such as to accelerate or decelerate the motor. For instance, the inverter bridge 4410 may brake the motor 4144 or cause sudden deceleration of the motor by reducing the effective voltage across the motor to a level below the back electromotive force (EMF) voltage of the motor. This process results in a reversal of the direction of the current so that the current flows from the inverter bridge 4410 towards the power supply 4210. More particularly, to brake the motor, a negative effective voltage is induced across the motor. The negative effective voltage causes current to reverse and flow back onto the bus or circuit lines between the power supply 4210 and the motor 4144, thereby raising the voltage level on the bus or circuit lines. The inverter bridge 4410 may also include a control connection such as a current signal between the motor and the remaining electronic components of the PAP device 4000 (e.g., a therapy device controller and/or a central controller).

As shown in FIG. 6, the inverter bridge may be controlled by the therapy device controller 4240. As described earlier, the therapy device controller 4240 may be a therapy control module that implements a part of the processes of the algorithms executed by the central controller 4230. For instance, as shown in FIG. 6, the central controller 4230 may control operation of the therapy device controller 4240, via provision of executable instructions, based on one or more input signals such as pressure, flow and temperature measurements received from the pressure transducer 4272, flow transducer 4274, and temperature transducer 4278, respectively. The transducers may be positioned to measure characteristics of the flow of breathable gas in the pneumatic path at various positions with respect to the blower 4142, such as, proximate to the outlet 4432 of the blower 4142.

The central controller 4230 may also receive the motor speed from the therapy device controller 4240. Depending on one or more various inputs, the central controller 4230 may adjust the blower 4142 output by instructing the therapy device controller 4240 to vary the current or voltage supplied to the motor 4144 through its control of the motor bridge.

With continued reference to FIG. 6, according to one aspect of the present technology, the transient absorption diode circuit 4400 may be disposed between the power supply 4210 and the inverter bridge 4410. Specifically, as shown in FIG. 6, the power supply 4210 may be coupled to the inverter bridge 4410 in a manner such that a first terminal 4212 of the power supply 4210 is coupled to a first terminal 4412 of the inverter bridge 4410 by a first line 4422 (e.g., a wire or signal line), and a second terminal 4214 of the power supply 4210 is coupled to a second terminal 4414 of the inverter bridge 4410 by a second line 4424. In some cases, the first line 4422 may be a direct current (DC) bus or line, whereas the second line 4424 may be a ground line, or vice versa.

As shown in FIG. 6, the transient absorption diode circuit 4400 is arranged between the power supply 4210 and the inverter bridge 4410 in a manner such that a first terminal 4402 of the transient absorption diode circuit 4400 is coupled to the first line 4422 and a second terminal 4404 of the transient absorption diode circuit 4400 is coupled to the second line 4424.

According to one embodiment, the transient absorption diode circuit 4400 may include one, two or more transient absorption diodes 4420. Examples of the transient absorption diodes 4420 may include transient voltage suppressor (TVS) diodes and Transil™, among other possibilities. The transient absorption diodes 4420 may be connected in series or in parallel to each other so as to serve together as a voltage clamp across the first line 4422 and the second line 4424. In particular, connecting the transient absorption diodes 4420 to each other in series allows for a more even distribution of energy absorption in each transient absorption diode 4420. In the example illustrated in FIG. 6, two transient absorption diodes 4420 (e.g., transient voltage suppressor diodes) are connected in series across the first line 4422 and the second line 4424. Additional transient absorption diodes 4420 may be added to the transient absorption diode circuit 4400 as necessary to handle increasing regenerative energy.

With such a configuration, energy generated by the motor 4144 during motor braking or sudden deceleration is dumped or diverted into the transient absorption diode circuit 4400. In this regard, a transient absorption diode may typically be understood to absorb external destructive spikes that are of a very high energy for a very short period of time, such as on the order of 10 s of microseconds. Nevertheless, in a typical application of the present technology, it has been determined that the transient absorption diode circuit 4400 may serve to suppress energy spikes (e.g., from a flow generator motor) when they are of a much smaller amount of energy even if lasting for a longer period of time, such as on the order of 100's of milliseconds. The transient absorption diode circuit 4400 may absorb energy at a predetermined rate such that the energy spikes may be suppressed over the longer period of time without causing temperature increase above acceptable limits at, for instance, the junctions of the circuit 4400. The use of two or more transient absorption diodes 4420 connected in series may spread the energy dissipation load, which, in turn, spread the heat over more copper of the printed circuit board (PCB), consequently, maintaining the temperature at the junctions of the circuit 4400 within acceptable limits.

According to another embodiment of the present technology as illustrated in FIG. 7, the transient absorption diode circuit 4400 may include one or more capacitors 4421 in addition to the transient absorption diodes 4420. The one or more capacitors 4421 may be connected, such as in parallel, with each other. The one or more capacitors 4421 may also be connected, such as in parallel, with the serially connected transient absorption diodes 4420. The one or more capacitors 4421 may serve to store at least a portion of the energy generated by the motor 4144 during brake or sudden deceleration. The stored energy may then be re-used to power components of the circuit such as the motor.

Potential Advantages of the Transient Absorption Diode Circuit 4400

Such transient absorption diode circuits may have multiple advantages. For instance, the transient absorption diode circuit 4400 may provide a simple cost effective approach for addressing the kinetic regenerative energy produced during motor braking or sudden motor deceleration.

For example, the transient absorption diode circuit 4400 may serve as an alternative to a more costly switched resistive load or switched resistor circuit that might be implemented. Such a switched resistive load or switched resistor circuit generally requires a significant amount of printed circuit board (PCB) footprint and demands a significant amount of cost in components, labour, and development time. Further, the switched resistor circuit method requires a control circuit which may add to the complexity, cost and failure modes. However, such a control circuit is not required when a transient absorption diode circuit is used. By displacing the switched resistive load or switched resistor circuit, a transient absorption diode circuit 4400 may significantly reduce PCB footprint, labour, development time, which, in turn, may significantly reduce the cost of goods sold or the cost per device.

Fault Mitigation Integrated Circuit 4500

According to one aspect of the present technology, a protection circuit 4250 may include a single integrated circuit or chip. Such a chip may be configured to perform fault detection. Operations of such an integrated circuit may be independent of and separate from the central controller 4230. However, such a circuit may be configured to provide fault information (e.g., one or more output signals) to such a central controller 4230. Such an integrated circuit may also serve as a fault mitigation integrated circuit (IC) 4500. An example of such a component is illustrated in FIGS. 8-9.

In some versions, the fault mitigation IC 4500 may be a mixed signal chip. Such a chip is configured to receive one or more signals, which may be analog as well as digital input signals. Input signal(s) received by the fault mitigation IC 4500 may represent one or more physical or system parameters of the PAP device 4000. Such physical or system parameters may include, but not limited to, one or more of the following: motor current, motor bus voltage, motor speed, pressure measurement, flow measurement, temperature measurement, and system reset signal.

The fault mitigation IC 4500 may rely on one or more of the physical or system parameters to detect if any undesirable or potentially dangerous condition, namely, fault, is present. The fault mitigation IC 4500 may be configured to detect different types of faults with respect to the PAP device 4000, including, but not limited to, (a) power failure such as no power or insufficient power, (b) operating parameters (e.g., pressure, flow, temperature, or $PaO_2$ measurements) outside the scope of recommended ranges, (c) failure of a test alarm to generate a detectable alarm signal, (d) malfunction with respect to any of the transducers including, for example, the pressure transducer 4272, the flow transducer 4274, the motor speed transducer 4276, and the temperature transducer 4278, and (e) failure to detect the presence of a component, among other possibilities.

Once a fault is detected, the fault mitigation IC 4500 may generate one or more signals (e.g., digital and/or analog) to shut down critical hardware. Examples of such critical hardware may include one or more of the following: the blower 4142, the motor 4144, the inverter bridge 4410, and the therapy device controller 4240, among other possibilities. Additionally or as an alternative, when a fault is detected, the fault mitigation IC 4500 may report the information representative of the detected fault to the central controller 4230 (e.g., by sending a digital interrupt signal).

Referring to FIGS. 8-11, the fault mitigation IC 4500 may generally include one or more of the following components: input and output pins to receive and output signals, programmable logic that implements mechanisms to determine a fault based on an evaluation of the received signals, and a timer or timers. Detailed discussion of each component follows.

Input Pins

The fault mitigation IC 4500 may include any number of input pins, e.g., eight input pins as illustrated in FIGS. 8-9. The fault mitigation IC 4500 may receive analog and digital input signals via one or more of the input pins. One or more of the input pins may be communicatively coupled to one or more components of the device 4000 to receive physical or system parameters of the device 4000. For instance, by coupling with various components of the device 4000, the input pins may receive input signals such as motor current, motor bus voltage, motor speed, pressure measurement, flow measurement, temperature measurement, and system reset signal.

By way of further example, as illustrated in FIG. 11, the input pin "IN1" may be communicatively coupled to the therapy device controller 4240 to receive the current supplied to the motor 4144, namely, demand current signal or motor current signal. The input pins "IN2" and "IN3" may also be communicatively coupled to the therapy device controller 4240 to receive the motor bus voltage signal and the motor speed signal, respectively. The input pin "IN4" may be coupled to the pressure transducer 4272 to receive the pressure measurement signal. The input pin "IN5" may be coupled to the flow transducer 4274 to receive the flow measurement signal. The input pin "IN6" may be coupled to the temperature transducer 4278 to receive the temperature measurement signal. The input pin "IN7" may be configured to receive a system reset signal. The system reset signal may be provided by the input devices 4220 (not shown in FIG. 11) or the central controller 4230.

The number of input pins shown in FIGS. 8-11 is for illustration purposes only. In fact, the fault mitigation IC 4500 may include any number of input pins, not necessarily limited to that shown in the figures, based on various needs or complexity of the implementation.

Output Pins

With reference to FIGS. 8-11, the fault mitigation IC 4500 may include any number of output pins, e.g., eight output pins. The fault mitigation IC 4500 may generate analog and/or digital signals via one or more of the output pins. In some embodiments, each output pin may produce a logic output that represents a binary value. When the logic output at an output pin is high, the corresponding binary value provided by that output pin may be regarded as "1." By contrast, when the logic output at an output pin is low, the corresponding binary value provided by that output pin may be regarded as "0."

Once a fault is detected, such as in accordance with the programmed logic of the chip, the fault mitigation IC 4500 may directly control, without software intervention such as of the central controller, some or all of the critical hardware of the device 4000 via one or more output signals. The fault mitigation IC 4500 may also report the detected fault to the central controller 4230 via one or more output signals. In some cases, the fault mitigation IC 4500 may implement the same output signal for control of the critical hardware of the device 4000 and to report fault information to the central controller 4230.

For example, in some embodiments, when a fault is detected, the fault mitigation IC 4500 may output a stop signal (which may also be referred to as an interrupt signal) via a digital output pin, e.g., "OUT1," and output the type of the detected fault via one or more remaining output pins, e.g., "OUT2," "OUT3," and "OUT4."

For instance, in the absence of detecting any fault, the logic output at the output pin "OUT1" may be set low with a binary value of "0." The device 4000 may then operate normally under this circumstance. In the event that a fault is detected, the logic output at the output pin "OUT1" may be set high with a binary value of "1," resulting in a stop signal.

The logic output at the output pin "OUT1" may serve multiple purposes. For instance, the output pin "OUT1" may be coupled to the therapy device controller 4240. When the logic output at the output pin "OUT1" is set low by the fault mitigation IC 4500, the therapy device controller 4240, the inverter bridge 4410 and the motor 4144 may continue their operations as normal. However, when the logic output at the output pin "OUT1" is set high by fault mitigation IC 4500, in other words, when the stop signal is generated, the therapy device controller 4240 may act accordingly to shut down operation of the motor 4144. One advantage of this arrangement may be that it allows the critical hardware components (such as the motor 4144) to be shut down without invoking any software process. In some instances, the output pin "OUT1" may issue a digital signal.

The output pin "OUT1" may also be coupled to the central controller 4230. When the logic output at the output pin "OUT1" remains low, the central controller 4230 may continue its normal operation. However, when the logic output at the output pin "OUT1" becomes high, the stop signal is generated so as to interrupt the central controller 4230. Once the central controller 4230 receives the stop signal, the central controller 4230 may act accordingly, such as accessing the fault mitigation IC 4500 by retrieving or evaluating signal information regarding the detected fault type.

In some embodiments, the stop signal produced by the output pin "OUT1" controls operations of both the motor 4144 and the central controller 4230 simultaneously.

Still further, when a fault is detected, the fault mitigation IC 4500 may indicate the type of the detected fault at one or more remaining output pins. For instance, the fault mitigation IC 4500 may set the logic output of one or more output pins to indicate the type of the detected fault. In one example, the fault mitigation IC 4500 may drive multiple output pins (e.g., "OUT2," "OUT3," and "OUT4") to indicate the fault type. FIG. 12 is a table 4560 with an example association between fault types and different output combinations of the output pins "OUT2," "OUT3," and "OUT4." As shown in FIG. 12, when the binary values at all three output pins are "0," no fault type is indicated. However, when the binary values at the output pins "OUT2," "OUT5," and "OUT4" are "0," "0," and "1," respectively, the detected fault type is overpressure. Thus, as shown in FIG. 12, a 3-bit binary code via three digital output pins may provide eight different types of faults. Of course, the fault mitigation IC 4500 may engage a greater or lesser number of output pins to represent a greater or lesser number of different types of fault. Optionally, such output may be represented by one or more analog signal(s). The number of different types of faults expressed by the output pins is two to the power of the number of output pins used. For example, a 2-bit binary code via two digital output pins provides four different types of faults as $2^2=4$, and a 4-bit binary code via four digital output pins provides sixteen different types of faults as $2^4=16$.

When a fault is detected, the fault mitigation IC 4500 may change the logic outputs at the various output pins, e.g., "OUT1," "OUT2," "OUT3," and "OUT4," simultaneously. Specifically, the fault mitigation IC 4500 may generate the stop signal and indicate the type of fault at various output pins at the same time. As such, the detected fault type is readily accessible to the central controller 4230, when the central controller 4230 is interrupted by the stop signal. Accordingly, once interrupted, the central controller 4230 may read the fault type from signals of the output pins, e.g., "OUT2," "OUT3," and "OUT4," and then respond accordingly such as by changing operational control of the device, recording the fault and/or presenting a warning or message of the fault on a display device or via an electronic communication.

In some embodiments, when the fault mitigation IC 4500 receives a system reset signal, the fault mitigation IC 4500 may clear logic outputs at all the output pins, for instance, by setting the logic output at each output pin to low, i.e., to a binary value of "0."

The number of output pins shown in FIGS. 8-11 is for illustration purposes only. In fact, the fault mitigation IC 4500 may include any number of output pins, not necessarily limited to that shown in the figures, based on various needs or complexity of the implementation.

Programmable Logic

As shown in FIG. 10, the fault mitigation IC 4500 may include one or more programmable logic devices (PLD) with programmable logic 4510 that implements fault detection algorithms. A suitable programmable logic device may, for example, be implemented with programmable logic cells or a programmable logic array.

In some cases, the programmable logic device may be implemented with PLD semiconductors. Such devices may be selectively configurable but are typically much smaller than software processors and may be considered more reliable. For instance, the programmable logic device may include a programmable read-only memory core. The programmable logic device may also include arrays of transistor cells that implement logic functions, such as complex fault mitigation algorithms. The arrays of transistor cells may implement binary logic equations for each of the outputs in terms of the inputs or the logical complements of the inputs obtained via inverters 4514. As seen in FIG. 10, various output pins may be driven by the programmable logic 4510 based on inputs received from the various input pins.

The programmable logic 4510 may implement logic functions to detect different types of fault with the PAP device 4000. For instance, the programmable logic 4510 may detect one or more given operating parameters, or any combination thereof being out of an expected range or ranges. By way of example, the programmable logic 4510 may detect an overpressure condition when the measured pressure exceeds an overpressure threshold or exceeds an expected pressure range. The overpressure threshold or expected pressure range may be predetermined or otherwise set within the programmable logic. As shown in FIG. 11, the programmable logic 4510 may obtain the measured pressure via an input pin, e.g., "IN4," and compare the measured pressure to the threshold or expected range. If the measured pressure is too high, such as exceeding the overpressure threshold or exceeding the expected range, the operation of the motor 4144 may be deemed dangerous for a user. As a result, the fault mitigation IC 4500 may produce the stop signal via an output pin, e.g., "OUT1," to indicate the detection of a fault. At the same time, the fault mitigation IC 4500 may set the detected fault type, e.g., a stall or overpressure condition, at one or more remaining output pins. For instance, the logic outputs or signals at the output pins "OUT2," "OUT3," and "OUT4" may be set to binary values "0," "0," "1," respectively, to indicate overpressure as the detected fault type.

Similarly, the programmable logic 4510 may also determine whether the measured pressure falls below an under pressure threshold or an expected pressure range. If that is the case, the programmable logic 4510 may output under pressure as the detected fault type.

By contrast, if the measured pressure falls within the expected pressure range, the pressure transducer 4272 may be deemed suitable for normal operation of the device 4000. As such, no fault is detected. The logic output at the output pin used for reporting a fault, e.g., "OUT1," may remain low. In that regard, the device 4000 including the central controller 4230, the therapy device controller 4240, the inverter bridge 4410, and the motor 4144 may continue their normal operations.

The programmable logic 4510 may also be implemented with logic to detect other types of fault, such as whether a measurement of motor current, motor bus voltage, motor speed, flow, or temperature exceeds the respective threshold or expected range.

Timer

As illustrated in FIG. 10, the fault mitigation IC 4500 may include one or more timers 4512. The one or more timers 4512 may be internal to the programmable logic 4510 as shown in FIG. 10 or it may be external to the programmable logic 4510. Such a timer 4512 may be highly configurable, and may facilitate the implementation of complex, time dependent fault mitigation methodologies. A timer 4512 may generate a clock signal.

Latch

As illustrated in FIG. 10, the fault mitigation IC 4500 may include one or more latches 4520 disposed between the programmable logic 4510 and the output pins. A latch 4520 may also be referred to as flip-flop configured to store state information. A latch 4520 may be of different types, including but not limited to, a simple set-reset latch (e.g., SR NOR latch, SR NAND latch, JK latch), a gated latch (e.g., Gated SR latch, Gated D latch, Earle latch), a D flip-flop, a T flip-flop, and a JK flip-flop, among other possibilities.

In one example as illustrated in FIG. 10, the latches 4520 are D flip-flops. Each latch 4520 may receive a clock signal, e.g., from the timer 4512. When the programmable logic 4510 generates a signal on the D input pin of a latch 4520, that signal may be captured and locked by the latch 4520. Any subsequent changes on the D input pin may be ignored until the next clock event.

Example Operation

In operation, with reference to FIG. 11, the fault mitigation IC 4500 may monitor physical and system parameters of the device 4000, including among others, motor current, motor bus voltage, motor speed, pressure, flow, temperature, and system reset. Based on one or more of these parameters, the fault mitigation IC 4500 may determine whether a hazardous situation is imminent, namely, whether a fault is present. If so, the fault mitigation IC 4500 may shut down the motor 4144 to prevent the occurrence of, or ameliorate hazardous conditions that may compromise the safety of the user and/or the device 4000.

For instance, once a fault is detected, the fault mitigation IC 4500 may latch a single digital output signal at an output pin, e.g., "OUT1." This single digital output signal may shut down the therapy device controller 4240. As a result, the motor 4144 will stop.

The same single digital output signal may be applied via a signal branch line to also interrupt the central controller 4230 to signal that a fault has occurred.

Further, when a fault is detected, the fault mitigation IC 4500 may latch one or more signals at one or more remaining output pins, e.g., "OUT2," "OUT3," and "OUT4," to report the type of fault as detected. The programmable logic 4510 may determine the fault type, and set binary values corresponding to the fault type on the output pins accordingly.

In some embodiments, one or more of the output pins of the fault mitigation IC 4500 may remain latched until the power of the system is cycled, or until a system reset signal is received. The system reset signal may release the latch, reset the fault mitigation IC 4500, or reset the device 4000 as a whole. Thus, for example, the stop signal to shut down the operation of the motor 4144 may be substantially maintained to protect against continued use of the flow generator.

In some versions, the fault mitigation IC 4500 may be configured to detect fault(s) prior to the therapeutic treatment to the patient, such as part of an initiation procedure. Additionally, or alternatively, the fault mitigation IC 4500 may detect fault periodically or continuously during the therapeutic treatment to the patient.

Potential Advantages of the Fault Mitigation Integrated Circuit 4500

The fault mitigation IC 4500 may have multiple advantages. First, implementation as a single integrated circuit replaces the needs for discrete electronic parts, components, or other circuit elements that otherwise would be used to perform fault detection. Discrete electronic parts, components, or circuits may generally require a greater amount of printed circuit board (PCB) footprint and demand a significant amount of cost in components, labour, and development time. By displacing the discrete electronic parts, components or circuits, the fault mitigation IC 4500 may significantly reduce PCB footprint, labour, and development time, which, in turn, may reduce the cost of goods sold or the cost per device.

Second, since the programmable logic 4510 of the fault mitigation IC 4500 is highly configurable, the product development time may be reduced. Also due to its highly configurable nature, the fault mitigation IC 4500 may be easily configured and reconfigured to detect various types of fault.

Third, the fault mitigation IC 4500 implements the fault detection algorithms using hardware alone, and obviates any need for software implementations. As such, the safety of the device 4000 is significantly enhanced.

Further, the fault mitigation IC 4500 may perform fault detection independent of and separate from the central controller 4230, which, in turn, simplifies the implementation of the central controller 4230.

PAP Device Algorithms

As previously mentioned, the central controller may be implemented with algorithms in processes to implement the functions of a respiratory treatment. Any one or more of the following example process modules may be included.

Pre-Processing Module 4310

With reference to FIG. 4*d*, a pre-processing module 4310 in accordance with the present technology receives as an input, raw data from a transducer, for example a pressure transducer 4272 or a flow transducer 4274, and preferably performs one or more process steps to calculate one or more output values that will be used as an input to another module, for example a therapy engine module 4320.

In one form of the present technology, the output values include the interface or mask pressure $Pm$, the respiratory flow $Qr$, and the leak flow $Ql$.

In various forms of the present technology, the pre-processing module 4310 comprises one or more of the following algorithms: pressure compensation algorithm 4312, vent flow algorithm 4314, leak flow algorithm 4316, respiratory flow algorithm 4318, and jamming detection algorithm 4319.

Pressure Compensation

In one form of the present technology, a pressure compensation algorithm 4312 (shown in FIG. 4*d*) receives as an input a signal indicative of the pressure in the pneumatic path proximal to an outlet of the pneumatic block. The pressure compensation algorithm 4312 estimates the pressure drop in the air circuit 4170 and provides as an output an estimated pressure, $Pm$, in the patient interface 3000.

Vent Flow

In one form of the present technology, a vent flow algorithm 4314 (shown in FIG. 4d) for vent flow calculation receives as an input an estimated pressure, Pm, in the patient interface 3000 and estimates a vent flow of air, Qv, from a vent 3400 in a patient interface 3000.

Leak Flow

In one form of the present technology, a leak flow algorithm 4316 (shown in FIG. 4d) receives as an input a total flow, Qt, and a vent flow Qv, and provides as an output a leak flow Ql by calculating an average of Qt-Qv over a period sufficiently long to include several breathing cycles, e.g. about 10 seconds.

In one form, the leak flow algorithm 4316 receives as an input a total flow, Qt, a vent flow Qv, and an estimated pressure, Pm, in the patient interface 3000, and provides as an output a leak flow Ql by calculating a leak conductance, and determining a leak flow Ql to be a function of leak conductance and interface pressure, Pm. In one implementation, leak conductance is calculated as the quotient of low pass filtered non-vent flow Qt-Qv, and low pass filtered square root of mask pressure Pm, where the low pass filter time constant has a value sufficiently long to include several breathing cycles, e.g. about 10 seconds.

Respiratory Flow

In one form of the present technology, a respiratory flow algorithm 4318 receives as an input a total flow, Qt, a vent flow, Qv, and a leak flow, Ql, and estimates a respiratory flow to the patient, Qr, by subtracting the vent flow Qv and the leak flow Ql from the total flow Qt.

Jamming Detection

When the leak has recently changed and the leak flow algorithm 4316 has not fully compensated for the change, a state designated as "jamming" exists, which may be determined according to the methods described in U.S. Pat. Nos. 6,532,957, 6,810,876 or U.S. Patent Application Publication No. 2010/0101574 A1, the disclosures of which are incorporated herein by reference. In the jamming state, the respiratory flow baseline is usually incorrect to some degree, which distorts flow shapes and affects the detection of flow limitation. Jamming, which may be taken to represent an extent of uncompensated leak, is calculated by the jamming detection algorithm 4319 (shown in FIG. 4d).

Therapy Engine Module 4320

In one form of the present technology, a therapy engine module 4320 (shown in FIG. 4d) receives as inputs one or more of a pressure, Pm, in a patient interface 3000, a respiratory flow of air to a patient, Qr, a leak flow, Ql, a jamming variable and provides as an output, one or more therapy parameters.

In some versions of the present technology, a therapy parameter is a CPAP treatment pressure Pt or a bi-level pressure treatment.

In one form of the present technology, a therapy parameter is one or more of a level of pressure support, and a target ventilation.

Phase Determination

In one form of the present technology, the PAP device 4000 does not determine phase.

In one form of the present technology, a phase determination algorithm 4321 (shown in FIG. 4d) receives as an input a signal indicative of respiratory flow, Qr, and provides an estimate Φ of the phase of a breathing cycle of the patient 1000. The rate of change of phase is indicative of the respiratory rate.

Waveform Determination

In one form of the present technology, a therapy control module 4330 controls a therapy device 4245 to provide an approximately constant positive airway pressure throughout a respiratory cycle of a patient.

In one form of the present technology, a therapy control module 4330 controls a therapy device 4245 to provide positive airway pressure according to a predetermined waveform of pressure versus phase. In one form, the waveform is maintained at an approximately constant level for all values of phase. In one form, the waveform is a square wave, having a higher value for some values of phase, and a lower level for other values of phase.

In one form of the present technology a waveform determination algorithm 4322 (shown in FIG. 4d) receives as an input a value indicative of current patient ventilation, Vent, and provides as an output a waveform of pressure vs. phase.

In one form, the waveform is a square wave, having a value of 1 for early values of phase corresponding to inspiration, and a value of 0 for later values of phase corresponding to expiration. In other forms, the waveform is a more "smooth and comfortable" waveform with a gradual rise to 1 for early values of phase, and a gradual fall to 0 for later values of phase.

Ventilation Determination

In one form of the present technology, a ventilation determination algorithm 4323 (shown in FIG. 4d) receives an input a respiratory flow Qr, and determines a measure indicative of patient ventilation, Vent.

In one form ventilation determination algorithm 4323 determines a current value of patient ventilation, Vent, as the half the low-pass filtered absolute value of respiratory flow, Qr.

Determination of Inspiratory Flow Limitation

In one form of the present technology, a processor executes one or more Inspiratory Flow limitation algorithms 4324 (shown in FIG. 4d) for the detection of inspiratory flow limitation.

In one form the inspiratory flow limitation algorithm 4324 receives as an input a respiratory flow signal Qr and provides as an output a metric of the extent to which the inspiratory portion of the breath exhibits inspiratory flow limitation.

The inspiratory flow limitation algorithm 4324 computes measures of at least one of the following three types of inspiratory flow limitation: ordinary flatness, M-shape, and "reverse chairness".

Detection of Apneas and Hypopneas

In one form of the present technology, a central controller 4230 executes one or more apneas and/or hypopneas algorithms 4325 (shown in FIG. 4d) for the detection of apneas and/or hypopneas.

Detection of Snore

In one form of the present technology, a central controller 4230 executes one or more snore algorithms 4326 (shown in FIG. 4d) for the detection of snore.

Determination of EPAP

In one form of the present technology, a number of different features indicative of upper airway obstruction ("UAO"), if present, cause a rise in the EPAP above a pre-set minimum value minimum EPAP, to a degree which is broadly proportional to the severity of the upper airway obstruction. When no features indicative of UAO are present, the EPAP decays progressively towards the pre-set minimum EPAP. This decay tends to minimise the EPAP delivered. At any given time, the EPAP is a balance between the forces tending to make it rise and the tendency to decay. An approximate equilibrium may be reached in which occasional indicators of mild UAO cause upward movements in EPAP which are counterbalanced by the decay that occurs when there are no indicators of UAO.

When the EPAP adjustment algorithm 4327 (shown in FIG. 4d) prescribes an increase in EPAP, that increase may not occur instantaneously. Such rises in EPAP may be controlled by the central controller 4230 and timed to occur only during what the PAP device 4000 considers to be inspiration. An example of such a technique is disclosed in U.S. Patent Application Publication No. 2011/0203588 A1, the disclosure of which is incorporated herein by reference.

Determination of Target Ventilation 4328

In some cases, a target ventilation may be set to a percentage (e.g., 90%) of the typical recent ventilation calculated as the output of a first-order low pass filter with time constant 3 minutes (the ventilation filter) that is applied to the instantaneous ventilation.

Determination of Therapy Parameters

The central controller 4230 executes one or more algorithms 4329 (shown in FIG. 4d) for the determination of therapy parameters.

Control Module 4330

A therapy control module 4330 in accordance with one form of the present technology receives as an input a target treatment pressure Pt, and controls a therapy device 4245 to deliver that pressure.

A therapy control module 4330 in accordance with another form of the present technology receives as inputs an EPAP, a waveform value, and a level of pressure support, computes a target treatment pressure Pt, and controls a therapy device 4245 to deliver that pressure.

A therapy control module 4330 in accordance with another form of the present technology receives as an input an EPAP, a waveform value, a target ventilation, and an instantaneous ventilation, computes a level of pressure support from the target ventilation and the instantaneous ventilation, computes a target treatment pressure Pt using the EPAP, the waveform value, and the pressure support, and controls a therapy device 4245 to deliver that pressure.

Detection of Fault Conditions

In one form of the present technology, a central controller 4230 may execute one or more methods for the detection of fault conditions. The fault conditions detected by the one or more methods may include at least one of the following:

Power failure (no power, or insufficient power)
Transducer fault detection
Failure to detect the presence of a component
Operating parameters outside recommended ranges (e.g. pressure, flow, temperature, $PaO_2$)
Failure of a test alarm to generate a detectable alarm signal.

Upon detection of the fault condition, the corresponding algorithm signals the presence of the fault by one or more of the following:

Initiation of an audible, visual and/or kinetic (e.g. vibrating) alarm
Sending a message to an external device
Logging of the incident According to another aspect of the present technology, the central controller 4230 may omit a software module for detecting fault conditions. Rather, as discussed earlier, the detection of fault conditions may be handled exclusively by the fault mitigation integrated circuit 4500 that is separate from the central controller 4230. In some cases, the fault mitigation integrated circuit 4500 may serve as a redundant backup to similar fault detection/mitigation module with algorithms processed also within the central controller.

Therapy Device 4245

In a preferred form of the present technology, the therapy device 4245 (shown in FIG. 4c) is under the control of the therapy control module 4330 to deliver therapy to a patient 1000.

Preferably the therapy device 4245 is a positive air pressure device 4140.

Humidifier 5000

In one form of the present technology there is provided a humidifier 5000 (shown in FIG. 5) comprising a water reservoir and a heating plate.

GLOSSARY

For the purposes of the present technology disclosure, in certain forms of the present technology, one or more of the following definitions may apply. In other forms of the present technology, alternative definitions may apply.

General

Air:

In certain forms of the present technology, air supplied to a patient may be atmospheric air, and in other forms of the present technology atmospheric air may be supplemented with oxygen.

Continuous Positive Airway Pressure (CPAP):

CPAP treatment will be taken to mean the application of a supply of air or breathable gas to the entrance to the airways at a pressure that is continuously positive with respect to atmosphere, and preferably approximately constant through a respiratory cycle of a patient. In some forms, the pressure at the entrance to the airways will vary by a few centimetres of water within a single respiratory cycle, for example being higher during inhalation and lower during exhalation. In some forms, the pressure at the entrance to the airways will be slightly higher during exhalation, and slightly lower during inhalation. In some forms, the pressure will vary between different respiratory cycles of the patient, for example being increased in response to detection of indications of partial upper airway obstruction, and decreased in the absence of indications of partial upper airway obstruction.

Aspects of Pap Devices

Air Circuit:

A conduit or tube constructed and arranged in use to deliver a supply of air or breathable gas between a PAP device and a patient interface. In particular, the air circuit may be in fluid connection with the outlet of the pneumatic block and the patient interface. The air circuit may be referred to as air delivery tube. In some cases there may be separate limbs of the circuit for inhalation and exhalation. In other cases a single limb is used.

APAP:

Automatic Positive Airway Pressure. Positive airway pressure that is continually adjustable between minimum and maximum limits, depending on the presence or absence of indications of SDB events.

Blower or Flow Generator:

A device that delivers a flow of air at a pressure above ambient pressure.

Controller:

A device or portion of a device that adjusts an output based on an input. For example one form of controller has a variable that is under control—the control variable—that constitutes the input to the device. The output of the device is a function of the current value of the control variable, and a set point for the variable. A servo-ventilator may include a controller that has ventilation as an input, a target ventilation as the set point, and level of pressure support as an output. Other forms of input may be one or more of oxygen saturation (SaO2), partial pressure of carbon dioxide (PCO2), movement, a signal from a photoplethysmogram, and peak flow. The set point of the controller may be one or more of fixed, variable or learned. For example, the set point in a ventilator may be a long term average of the measured ventilation of a patient. Another ventilator may have a ventilation set point that changes with time. A pressure controller may be configured to control a blower or pump to deliver air at a particular pressure.

Therapy:

Therapy in the present context may be one or more of positive pressure therapy, oxygen therapy, carbon dioxide therapy, control of dead space, and the administration of a drug.

Motor:

A device for converting electrical energy into rotary movement of a member. In the present context the rotating member is an impeller, which rotates in place around a fixed axis so as to impart a pressure increase to air moving along the axis of rotation.

Positive Airway Pressure (PAP) Device:

A device for providing a supply of air at positive pressure to the airways.

Transducers:

A device for converting one form of energy or signal into another. A transducer may be a sensor or detector for converting mechanical energy (such as movement) into an electrical signal. Examples of transducers include pressure sensors, flow sensors, carbon dioxide ($CO_2$) sensors, oxygen ($O_2$) sensors, effort sensors, movement sensors, noise sensors, a plethysmograph, and cameras.

Volute:

The casing of the centrifugal pump that receives the air being pumped by the impeller, slowing down the flow rate of air and increasing the pressure. The cross-section of the volute increases in area towards the discharge port.

Aspects of the Respiratory Cycle

Apnea:

An apnea will be said to have occurred when flow falls below a predetermined threshold for a period of duration, e.g. 10 seconds. An obstructive apnea will be said to have occurred when, despite patient effort, some obstruction of the airway does not allow air to flow. A central apnea will be said to have occurred when an apnea is detected that is due to a reduction in breathing effort, or the absence of breathing effort.

Breathing Rate:

The rate of spontaneous respiration of a patient, usually measured in breaths per minute.

Duty Cycle:

The ratio of inhalation time, Ti to total breath time, Ttot.

Effort (Breathing):

Preferably breathing effort will be said to be the work done by a spontaneously breathing person attempting to breathe.

Expiratory Portion of a Breathing Cycle:

The period from the start of expiratory flow to the start of inspiratory flow.

Flow Limitation:

Preferably, flow limitation will be taken to be the state of affairs in a patient's respiration where an increase in effort by the patient does not give rise to a corresponding increase in flow. Where flow limitation occurs during an inspiratory portion of the breathing cycle it may be described as inspiratory flow limitation. Where flow limitation occurs during an expiratory portion of the breathing cycle it may be described as expiratory flow limitation.

Types of flow limited inspiratory waveforms:

(i) Flattened: Having a rise followed by a relatively flat portion, followed by a fall.

(ii) M-shaped: Having two local peaks, one at the leading edge, and one at the trailing edge, and a relatively flat portion between the two peaks.

(iii) Chair-shaped: Having a single local peak, the peak being at the leading edge, followed by a relatively flat portion.

(iv) Reverse-chair shaped: Having a relatively flat portion followed by single local peak, the peak being at the trailing edge.

Hypopnea:

Preferably, a hypopnea will be taken to be a reduction in flow, but not a cessation of flow. In one form, a hypopnea may be said to have occurred when there is a reduction in flow below a threshold for a period of duration. In one form in adults, the following either of the following may be regarded as being hypopneas:

(i) a 30% reduction in patient breathing for at least 10 seconds plus an associated 4% desaturation; or (ii) a reduction in patient breathing (but less than 50%) for at least 10 seconds, with an associated desaturation of at least 3% or an arousal.

Inspiratory Portion of a Breathing Cycle:

Preferably the period from the start of inspiratory flow to the start of expiratory flow will be taken to be the inspiratory portion of a breathing cycle.

Patency (Airway):

The degree of the airway being open, or the extent to which the airway is open. A patent airway is open. Airway patency may be quantified, for example with a value of one (1) being patent, and a value of zero (0), being closed.

Positive End-Expiratory Pressure (PEEP):

The pressure above atmosphere in the lungs that exists at the end of expiration.

Peak Flow (Qpeak):

The maximum value of flow during the inspiratory Portion of the Respiratory Flow Waveform.

Respiratory flow, airflow, patient airflow, respiratory airflow (Qr):

These synonymous terms may be understood to refer to the PAP device's estimate of respiratory airflow, as opposed to "true respiratory flow" or "true respiratory airflow", which is the actual respiratory flow experienced by the patient, usually expressed in litres per minute.

Tidal Volume (Vt):

The volume of air inhaled or exhaled during normal breathing, when extra effort is not applied.

(inhalation) Time (Ti):

The duration of the inspiratory portion of the respiratory flow waveform.

(Exhalation) Time (Te):

The duration of the expiratory portion of the respiratory flow waveform.

(Total) Time (Ttot):

The total duration between the start of the inspiratory portion of one respiratory flow waveform and the start of the inspiratory portion of the following respiratory flow waveform.

Typical Recent Ventilation:

The value of ventilation around which recent values over some predetermined timescale tend to cluster, that is, a measure of the central tendency of the recent values of ventilation.

Upper Airway Obstruction (UAO):

includes both partial and total upper airway obstruction. This may be associated with a state of flow limitation, in which the level of flow increases only slightly or may even decrease as the pressure difference across the upper airway increases (Starling resistor behaviour).

Ventilation (Vent):

A measure of the total amount of gas being exchanged by the patient's respiratory system, including both inspiratory and expiratory flow, per unit time. When expressed as a volume per minute, this quantity is often referred to as "minute ventilation". Minute ventilation is sometimes given simply as a volume, understood to be the volume per minute.

Pap Device Parameters

Flow Rate:

The instantaneous volume (or mass) of air delivered per unit time. While flow rate and ventilation have the same dimensions of volume or mass per unit time, flow rate is measured over a much shorter period of time. Flow may be nominally positive for the inspiratory portion of a breathing cycle of a patient, and hence negative for the expiratory portion of the breathing cycle of a patient. In some cases, a reference to flow rate will be a reference to a scalar quantity, namely a quantity having magnitude only. In other cases, a reference to flow rate will be a reference to a vector quantity, namely a quantity having both magnitude and direction. Flow will be given the symbol Q. Total flow, Qt, is the flow of air leaving the PAP device. Vent flow, Qv, is the flow of air leaving a vent to allow washout of exhaled gases. Leak flow, Ql, is the flow rate of unintentional leak from a patient interface system. Respiratory flow, Qr, is the flow of air that is received into the patient's respiratory system.

Leak:

Preferably, the word leak will be taken to be a flow of air to the ambient. Leak may be intentional, for example to allow for the washout of exhaled $CO_2$. Leak may be unintentional, for example, as the result of an incomplete seal between a mask and a patient's face.

Pressure:

Force per unit area. Pressure may be measured in a range of units, including $cmH_2O$, $g-f/cm^2$, and hectopascal. $1cmH_2O$ is equal to 1 $g-f/cm^2$ and is approximately 0.98 hectopascal. In this specification, unless otherwise stated, pressure is given in units of $cmH_2O$. For nasal CPAP treatment of OSA, a reference to treatment pressure is a reference to a pressure in the range of about 4-20 $cmH_2O$, or about 4-30 $cmH_2O$. The pressure in the patient interface is given the symbol Pm.

Sound Power:

The energy per unit time carried by a sound wave. The sound power is proportional to the square of sound pressure multiplied by the area of the wavefront. Sound power is usually given in decibels SWL, that is, decibels relative to a reference power, normally taken as $10^{-12}$ watt.

Sound Pressure:

The local deviation from ambient pressure at a given time instant as a result of a sound wave travelling through a medium. Sound power is usually given in decibels SPL, that is, decibels relative to a reference power, normally taken as $20 \times 10^{-6}$ Pascal (Pa), considered the threshold of human hearing.

Terms for Ventilators

Adaptive Servo-Ventilator:

A ventilator that has a changeable, rather than fixed target ventilation. The changeable target ventilation may be learned from some characteristic of the patient, for example, a respiratory characteristic of the patient.

Backup Rate:

A parameter of a ventilator that establishes the minimum respiration rate (typically in number of breaths per minute) that the ventilator will deliver to the patient, if not otherwise triggered.

Cycled:

The termination of a ventilator's inspiratory phase. When a ventilator delivers a breath to a spontaneously breathing patient, at the end of the inspiratory portion of the breathing cycle, the ventilator is said to be cycled to stop delivering the breath.

EPAP (or EEP):

a base pressure, to which a pressure varying within the breath is added to produce the desired mask pressure which the ventilator will attempt to achieve at a given time.

IPAP:

desired mask pressure which the ventilator will attempt to achieve during the inspiratory portion of the breath.

Pressure Support:

A number that is indicative of the increase in pressure during ventilator inspiration over that during ventilator expiration, and generally means the difference in pressure between the maximum value during inspiration and the minimum value during expiration (e.g., PS=IPAP−EPAP). In some contexts pressure support means the difference which the ventilator aims to achieve, rather than what it actually achieves.

Servo-Ventilator:

A ventilator that measures patient ventilation has a target ventilation, and which adjusts the level of pressure support to bring the patient ventilation towards the target ventilation.

Spontaneous/Timed (S/T)—

A mode of a ventilator or other device that attempts to detect the initiation of a breath of a spontaneously breathing patient. If however, the device is unable to detect a breath within a predetermined period of time, the device will automatically initiate delivery of the breath.

Swing:

Equivalent term to pressure support.

Triggered:

When a ventilator delivers a breath of air to a spontaneously breathing patient, it is said to be triggered to do so at the initiation of the respiratory portion of the breathing cycle by the patient's efforts.

Ventilator:

A mechanical device that provides pressure support to a patient to perform some or all of the work of breathing.

Ventilator Inspiration and Ventilator Expiration:

The periods during which the ventilator considers that it should deliver pressures appropriate respectively to patient inspiration and expiration. Depending on the quality of patient-ventilator synchronisation, and the presence of upper airway obstruction, these may or may not correspond to actual patient inspiration or expiration.

Anatomy of the Respiratory System

Diaphragm:

A sheet of muscle that extends across the bottom of the rib cage. The diaphragm separates the thoracic cavity, containing the heart, lungs and ribs, from the abdominal cavity. As the diaphragm contracts the volume of the thoracic cavity increases and air is drawn into the lungs.

Larynx:

The larynx, or voice box houses the vocal folds and connects the inferior part of the pharynx (hypopharynx) with the trachea.

Lungs:

The organs of respiration in humans. The conducting zone of the lungs contains the trachea, the bronchi, the bronchioles, and the terminal bronchioles. The respiratory zone contains the respiratory bronchioles, the alveolar ducts, and the alveoli.

Nasal Cavity:

The nasal cavity (or nasal fossa) is a large air filled space above and behind the nose in the middle of the face. The nasal cavity is divided in two by a vertical fin called the nasal septum. On the sides of the nasal cavity are three horizontal outgrowths called nasal conchae (singular "concha") or turbinates. To the front of the nasal cavity is the nose, while the back blends, via the choanae, into the nasopharynx.

Pharynx:

The part of the throat situated immediately inferior to (below) the nasal cavity, and superior to the oesophagus and larynx. The pharynx is conventionally divided into three sections: the nasopharynx (epipharynx) (the nasal part of the pharynx), the oropharynx (mesopharynx) (the oral part of the pharynx), and the laryngopharynx (hypopharynx).

OTHER REMARKS

A portion of the disclosure of this patent document contains material which is subject to copyright protection. The copyright owner has no objection to the facsimile reproduction by anyone of the patent document or the patent disclosure, as it appears in the Patent and Trademark Office patent file or records, but otherwise reserves all copyright rights whatsoever.

Unless the context clearly dictates otherwise and where a range of values is provided, it is understood that each intervening value, to the tenth of the unit of the lower limit, between the upper and lower limit of that range, and any other stated or intervening value in that stated range is encompassed within the technology. The upper and lower limits of these intervening ranges, which may be independently included in the intervening ranges, are also encompassed within the technology, subject to any specifically excluded limit in the stated range. Where the stated range includes one or both of the limits, ranges excluding either or both of those included limits are also included in the technology.

Furthermore, where a value or values are stated herein as being implemented as part of the technology, it is understood that such values may be approximated, unless otherwise stated, and such values may be utilized to any suitable significant digit to the extent that a practical technical implementation may permit or require it.

Unless defined otherwise, all technical and scientific terms used herein have the same meaning as commonly understood by one of ordinary skill in the art to which this technology belongs. Although any methods and materials similar or equivalent to those described herein can also be used in the practice or testing of the present technology, a limited number of the exemplary methods and materials are described herein.

When a particular material is identified as being preferably used to construct a component, obvious alternative materials with similar properties may be used as a substitute. Furthermore, unless specified to the contrary, any and all components herein described are understood to be capable of being manufactured and, as such, may be manufactured together or separately.

It must be noted that as used herein and in the appended claims, the singular forms "a", "an", and "the" include their plural equivalents, unless the context clearly dictates otherwise.

All publications mentioned herein are incorporated by reference to disclose and describe the methods and/or materials which are the subject of those publications. The publications discussed herein are provided solely for their disclosure prior to the filing date of the present application. Nothing herein is to be construed as an admission that the present technology is not entitled to antedate such publication by virtue of prior invention. Further, the dates of publication provided may be different from the actual publication dates, which may need to be independently confirmed.

Moreover, in interpreting the disclosure, all terms should be interpreted in the broadest reasonable manner consistent with the context. In particular, the terms "comprises" and "comprising" should be interpreted as referring to elements, components, or steps in a non-exclusive manner, indicating that the referenced elements, components, or steps may be present, or utilized, or combined with other elements, components, or steps that are not expressly referenced.

The subject headings used in the detailed description are included only for the ease of reference of the reader and should not be used to limit the subject matter found throughout the disclosure or the claims. The subject headings should not be used in construing the scope of the claims or the claim limitations.

Although the technology herein has been described with reference to particular embodiments, it is to be understood that these embodiments are merely illustrative of the principles and applications of the technology. In some instances, the terminology and symbols may imply specific details that are not required to practice the technology. For example, although the terms "first" and "second" may be used, unless otherwise specified, they are not intended to indicate any order but may be utilised to distinguish between distinct elements. Furthermore, although process steps in the methodologies may be described or illustrated in an order, such an ordering is not required. Those skilled in the art will recognize that such ordering may be modified and/or aspects thereof may be conducted concurrently or even synchronously.

It is therefore to be understood that numerous modifications may be made to the illustrative embodiments and that other arrangements may be devised without departing from the spirit and scope of the technology.

The invention claimed is:

1. A respiratory apparatus comprising:
   a power supply coupled to a bus, the bus comprising a direct current line and a ground line;
   a blower configured to generate a flow of breathable gas, the blower including a motor powered by the power supply via the bus, wherein the motor generates energy at certain times during operation; and
   a transient absorption diode circuit that serves as a voltage clamp across the direct current line and the ground line, and absorbs energy generated due to deceleration of the motor at a predetermined rate, the transient absorption diode circuit being coupled to the direct current line of the bus and the ground line of the bus, and
   wherein a period of the deceleration of the motor is on an order of hundreds of milliseconds and wherein one or more transient absorption diodes of the transient absorption diode circuit are configured to absorb said energy of the period.

2. The apparatus of claim 1, further comprising one or more capacitors between the motor and the power supply to store at least a portion of the energy generated, the one or more capacitors being connected in parallel with the transient absorption diode circuit and coupled to the direct current line and the ground line to power a component on the bus with the stored portion of the energy generated.

3. The apparatus of claim 1, wherein the power supply includes a Mains powered switched-mode power supply.

4. The apparatus of claim 3, wherein the Mains powered switched-mode power supply blocks negative regenerative currents.

5. The apparatus of claim 1, wherein the motor is a brushless DC electric motor.

6. The apparatus of claim 1, wherein the respiratory apparatus is one of a positive airway pressure or a non-invasive ventilation apparatus.

7. The apparatus of claim 1, wherein the transient absorption diode circuit absorbs the generated energy during motor braking.

8. The apparatus of claim 1, further comprising a bridge circuit to operate the motor.

9. The apparatus of claim 8, wherein the transient absorption diode circuit is connected to the power supply in parallel to the bridge circuit.

10. The apparatus of claim 8 wherein the bridge circuit is an inverter bridge.

11. The apparatus of claim 8, wherein the bridge circuit includes at least one switching MOSFET.

12. The apparatus of claim 8, wherein the bridge circuit is configured to decelerate or brake the motor.

13. The apparatus of claim 8, further comprising a motor drive coupled to the bridge circuit to control operation of the motor.

14. The apparatus of claim 13, wherein the motor drive includes a brushless DC motor controller.

15. The apparatus of claim 8, wherein the power supply is coupled to the bridge circuit, wherein a first terminal of the power supply is coupled to a first terminal of the bridge circuit by the direct current line, and a second terminal of the power supply is coupled to a second terminal of the bridge circuit by the ground line.

16. The apparatus of claim 15, wherein the transient absorption diode circuit includes a first terminal coupled to the direct current line and a second terminal coupled to the ground line.

17. The apparatus of claim 1, wherein the energy generated by the motor is converted from rotational kinetic energy.

18. The apparatus of claim 1 wherein the transient absorption diode circuit includes a first transient absorption diode having a first end that is coupled to the direct current line of the bus, and a second transient absorption diode having a first end coupled to the ground line of the bus,
wherein a second end of the first transient absorption diode is coupled to a second end of the second transient absorption diode.

19. The apparatus of claim 18, wherein the first end of the first transient absorption diode is a cathode and the first end of the second transient absorption diode is an anode.

20. The apparatus of claim 18, wherein the second end of the first transient absorption diode is an anode and the second end of the second transient absorption diode is a cathode.

* * * * *